United States Patent
Lichtenstein

(10) Patent No.: US 10,639,404 B2
(45) Date of Patent: May 5, 2020

(54) WOUND DRESSING

(75) Inventor: Isaac Lichtenstein, Brooklyn, NY (US)

(73) Assignee: WOUND HEALING TECHNOLOGIES, LLC, Brooklyn, NY (US)

( * ) Notice: Subject to any disclaimer, the term of this patent is extended or adjusted under 35 U.S.C. 154(b) by 0 days.

(21) Appl. No.: 13/152,446

(22) Filed: Jun. 3, 2011

(65) Prior Publication Data

US 2011/0301556 A1  Dec. 8, 2011

Related U.S. Application Data

(63) Continuation of application No. 61/350,988, filed on Jun. 3, 2010.

(51) Int. Cl.
*A61F 13/00* (2006.01)
*A61M 1/00* (2006.01)
*A61F 13/06* (2006.01)

(52) U.S. Cl.
CPC ..... *A61M 1/0088* (2013.01); *A61F 13/00068* (2013.01); *A61F 13/069* (2013.01); *A61F 2013/0054* (2013.01); *A61F 2013/00157* (2013.01); *A61F 2013/00174* (2013.01); *A61F 2013/00412* (2013.01); *A61F 2013/00519* (2013.01); *A61F 2013/00536* (2013.01)

(58) Field of Classification Search
CPC .............. A61M 1/0088; A61M 1/0023; A61M 1/0058; A61M 1/0084; A61M 27/00; A61M 1/009; A61F 13/0068; A61F 13/023; A61F 2013/00536; A61F 2013/0054; A61F 2013/00748; A61F 13/00068; A61F 13/0023; A61F 2013/00174

USPC ......................................................... 604/319
See application file for complete search history.

(56) References Cited

U.S. PATENT DOCUMENTS

| | | | |
|---|---|---|---|
| 4,969,880 A * | 11/1990 | Zamierowski | ................ 604/305 |
| 5,100,396 A | 3/1992 | Zamierowski | |
| 5,261,893 A | 11/1993 | Zamierowski | |
| 5,527,293 A | 6/1996 | Zamierowski | |
| 5,636,643 A | 6/1997 | Argenta et al. | |
| 5,645,081 A | 7/1997 | Argenta et al. | |

(Continued)

OTHER PUBLICATIONS

"Hydrocolloid dressing," Wikipedia, Aug. 28, 2013, San Francisco, California.

*Primary Examiner* — Ariana Zimbouski
(74) *Attorney, Agent, or Firm* — Weiss & Arons LLP

(57) ABSTRACT

Apparatus and methods for providing a wound dressing are provided. A wound dressing according to the invention may preferably include a wound-fluid negative pressure treatment ("NPT") drain and a vacuum/drainage tube comprising a terminus associated with the NPT drain. The dressing may also include a fluid-absorbing/transferring material. The dressing may also include a contour-conforming draping layer for draping over a wound-bed. The draping layer may be in contact with at least a portion of the fluid-absorbing/transferring material. The dressing may also include a vapor sealant sheet that overlies at least a portion of the fluid-absorbing/transferring layer. The material may also include a tube-anchorage component that is in contact with at least a portion of the vapor sealant sheet. The tube-anchorage component may mechanically maintain placement of the NPT drain within the fluid-absorbing/transferring material.

13 Claims, 16 Drawing Sheets

(56) References Cited

U.S. PATENT DOCUMENTS

| | | | |
|---|---|---|---|
| 5,951,505 A * | 9/1999 | Gilman et al. | 602/41 |
| 6,071,267 A * | 6/2000 | Zamierowski | 604/289 |
| 6,117,111 A | 9/2000 | Fleischmann | |
| 6,142,982 A | 11/2000 | Hunt et al. | |
| 6,345,623 B1 | 2/2002 | Heaton et al. | |
| 6,398,767 B1 | 6/2002 | Fleischmann | |
| 6,553,998 B2 | 4/2003 | Heaton et al. | |
| 6,685,681 B2 | 2/2004 | Lockwood et al. | |
| 6,814,079 B2 | 11/2004 | Heaton et al. | |
| 7,004,915 B2 | 2/2006 | Boynton et al. | |
| 7,216,651 B2 | 5/2007 | Argenta et al. | |
| 7,338,482 B2 | 3/2008 | Lockwood et al. | |
| 7,520,872 B2 * | 4/2009 | Biggie et al. | 604/319 |
| 7,615,036 B2 | 11/2009 | Joshi et al. | |
| 7,779,625 B2 | 8/2010 | Joshi et al. | |
| 7,951,100 B2 | 5/2011 | Hunt et al. | |
| 8,152,785 B2 | 4/2012 | Vitaris | |
| 8,168,848 B2 | 5/2012 | Lockwood et al. | |
| 8,187,210 B2 | 5/2012 | Hunt et al. | |
| 8,188,331 B2 | 5/2012 | Barta et al. | |
| 8,202,261 B2 | 6/2012 | Kazala, Jr. et al. | |
| 8,460,255 B2 | 6/2013 | Joshi et al. | |
| 8,663,198 B2 | 3/2014 | Buan et al. | |
| 8,945,074 B2 | 2/2015 | Buan et al. | |
| 9,058,634 B2 | 6/2015 | Buan et al. | |
| 9,067,003 B2 | 6/2015 | Buan et al. | |
| 2004/0073151 A1 * | 4/2004 | Weston | 602/41 |
| 2004/0243073 A1 * | 12/2004 | Lockwood et al. | 604/313 |
| 2005/0228330 A1 * | 10/2005 | Barnes et al. | 602/54 |
| 2007/0032755 A1 * | 2/2007 | Walsh | 602/2 |
| 2009/0234306 A1 * | 9/2009 | Vitaris | 604/304 |
| 2009/0299251 A1 | 12/2009 | Buan | |
| 2009/0299306 A1 | 12/2009 | Buan | |
| 2010/0121229 A1 * | 5/2010 | Argenta | A61B 17/00234 601/6 |
| 2010/0305526 A1 * | 12/2010 | Robinson | A61M 1/0001 604/319 |
| 2011/0034892 A1 | 2/2011 | Buan | |
| 2011/0130712 A1 * | 6/2011 | Topaz | 604/23 |
| 2011/0144599 A1 | 6/2011 | Croizat et al. | |
| 2011/0172612 A1 | 7/2011 | Greener et al. | |
| 2011/0196278 A1 | 8/2011 | Svedman et al. | |
| 2012/0041403 A1 | 2/2012 | Bennett et al. | |
| 2012/0197229 A1 | 8/2012 | Buan et al. | |
| 2013/0096519 A1 * | 4/2013 | Blott et al. | 604/319 |
| 2013/0150814 A1 | 6/2013 | Buan | |

* cited by examiner

WOUND DRESSING

CROSS-REFERENCE TO RELATED APPLICATION

This application is a non-provisional application of U.S. Provisional Application No. 61/350,988, filed on Jun. 3, 2010, entitled "Wound Dressing."

FIELD OF TECHNOLOGY

Aspects of the disclosure relate to systems and methods for therapeutic dressing of medical wounds. In particular, the disclosure relates to apparatus and methods for therapeutic dressing of wounds for their treatment by negative pressure.

BACKGROUND

Prior to applying a negative pressure dressing, a wound (or other opened-flesh medical condition) is typically cleansed and debrided. Therapeutic treatment of a wound often also involves packing the wound-bed with sterile material. Such material may include gauze, foam or other suitable fluid-absorbing/transferring materials. Application of negative pressure to the packed wound-bed promotes wound-healing.

The term "negative pressure" as used herein refers to lower than ambient air pressure. Widespread clinical experience sets the range of values of negative pressure utilized in wound treatment. Negative pressure treatment (hereinafter referred to as NPT) of wounds has been practiced for more than a decade.

The clinically demonstrated promotion of wound-healing that may be achieved through NPT requires successful practitioner-preparation of the wound and surrounding site. Conventionally, preparation of a wound for NPT complicates the wound-packing procedure for both practitioner and patient.

In conventional preparation for NPT, a practitioner needs to pause the wound-packing procedure at an intermediate stage, with the base of the prepared wound covered but with the wound-bed only partly packed. An appropriately sized wound-fluid NPT drain is introduced into the partly packed wound-bed.

A typical wound-fluid NPT drain may include a hollow tube-like structure featuring transversely perforated walls. Such perforation provides access to the drain's hollow center, which may or may not be capped on one end. A tube for application of negative pressure and for drainage of exuded wound-fluid typically attaches to, or is integrally continuous with, the other end of the drain. This vacuum/drainage tube exits the wound-bed and extends beyond it.

The NPT drain is associated in situ with the initial packing material within the wound-bed. More specifically, the NPT drain is typically placed upon the gauze or inserted within the foam. Location and orientation of the drain within the confines of the wound-bed may affect the efficiency of drainage and the quality of wound-closing.

To maintain the NPT drain's placement and orientation, anchorage of the exiting vacuum/drainage tube may be required. The exiting tube is preferably anchored in close proximity to the wound. Typically, the vacuum/drainage tube is taped to the patient's perilesional and/or other wound-proximal skin.

Conventionally, maintenance of NPT drain-and-tube emplacement and orientation may complicate the remaining stages of the wound-packing procedure. A practitioner laying the remaining packing material into the wound-bed may need to exercise caution to accommodate the presence of the NPT drain-and-tube. Even with the vacuum/drainage tube skin-anchored close to the wound, manipulations involved in completing the wound-packing procedure may deleteriously shift the NPT drain-and-tube.

The fully-packed wound-bed, with the emplaced NPT drain and the exiting vacuum/drainage tube, is completely draped with a flexible covering. The draping material closely adheres to sufficient skin area surrounding the wound-site to produce a perimeter seal that remains airtight under NPT conditions of negative wound-bed air pressure.

Particular wound-sites featuring high degrees of local moistness and/or contouring, may present challenges to producing effective airtight perimeter sealing. Practitioner-preparation of the wound for NPT requires smoothly adhering the surface-conforming draping material to the wider site's contours, with minimal disturbance of the packing, drain or tube. Such a procedure may be difficult and time-consuming.

The draping must allow for egress of the vacuum/drainage tube from the vicinity of the wound-site. The tube-egress may be sealed at the edge of the draping material by taping both the draping material and the vacuum/drainage tube at the site of tube-egress to the patient's skin. Such additional taping may be painful to the patient.

The end of the vacuum/drainage tube may be configured to connect to tubing leading to a suitable NPT vacuum controller. Wound-fluid exudate is drained from the sealed, packed wound-bed through the tubing, to a collection/disposal vessel associated with the vacuum controller. Prior to its disposal, collected exudate may be monitored as to volume, volume per time, fluid and cellular composition, bacterial count and/or other parameter(s) of clinical interest.

The therapeutic advantages of NPT have been clinically demonstrated for a broad variety of wound types, including but not limited to burns, lacerations, bed sores, etc. Improved patient-outcomes—including acceleration of wound-healing, decrease of infection and of necrosis, and enhancement of wound-closure quality—have been repeatedly noted in clinical studies.

Attainment of the clinical benefits of NPT depends upon successful practitioner-preparation of the wound-bed, of the surrounding perilesional area, and of the wider site. The number and intricacy of conventional NPT-required manipulations may make it difficult for a lone practitioner to efficiently carry out the procedure (while practical and institutional constraints may limit the number of practitioners and aides available); may lead to the need to repeat part or all of the procedure so as to correct earlier errors and/or later shifting of components; may contribute to incomplete success of the procedure, depriving the patient of the full benefit of NPT.

In the treatment of a typical wound, the above steps may be repeatedly applied over several courses of NPT. (As used herein, the term "course of NPT" refers to all NPT sessions performed on a given wound with a given NPT dressing in place; the term "NPT session" refers to any specific length of time over which the NPT vacuum controller applies continuous and/or intermittent negative pressure.) Each course of NPT may include, at the outset, cleansing and assessment of the progressively smaller wound-bed, followed by application of the dressing. Inherent painfulness may attend repeated manipulations of the wound-bed and surrounding wound-site, compounding the difficulties and complications involved in preparation of a wound for NPT by conventional apparatus and methods.

It would be desirable, therefore, to provide apparatus and methods for streamlining and simplifying preparation of a wound-site for NPT.

SUMMARY

Apparatus and methods for streamlining and simplifying preparation of a wound-site for NPT are provided. Such apparatus may include a wound dressing. (The term "wound" as used herein includes surgical and traumatic wounds, as well as other medical conditions for which NPT may be beneficial, such as any burns, pressure sores, diabetic ulcers, open abdominal wounds, and other conditions.)

The following description identifies in more detail some aspects of exemplary structure according to the invention. Certain embodiments of apparatus according to the present invention may incorporate in a single dressing some or all of the following components:

1. A preferably airtight, flexible, contour-conforming draping layer. A wound-facing broad surface of such draping may be capable of suitably adhering even to moist tissue surfaces; the same or another surface of such draping that may serve as a platform for other components. A drape may be selectively transversely perforated for transfer of air and/or fluid between the two surfaces; there may be one or more areas of such perforations across the draping layer.

2. One or more wound-fluid NPT drain(s). An NPT drain may be closely associated with and/or partly surrounded by one or more sets of layers of fluid-absorbing/transferring material(s) such as those suitable for wound-packing. Such sets of drain-associated surrounding material(s) may facilitate air/fluid transfer. Such transfer between an NPT drain and a prepared wound may be through draping layer perforations and via the drain-associated surrounding material(s); the area of a set of drain-associated surrounding material(s) may be nominally centered on an area of the draping layer perforations, facilitating such transfer. An NPT drain of the dressing according to the present invention may have functions and capabilities beyond the air/fluid transfer delineated in this paragraph.

3. One or more single-lumen or multi-lumen vacuum/drainage tube(s). One end of a vacuum/drainage tube may be associated with one or more wound-fluid NPT drains; the other end of a vacuum/drainage tube may be equipped with one or more airtight tube-connecting adapters for connection to an NPT vacuum controller and/or other treatment control-and-monitor equipment.

4. One or more preferably airtight vapor sealant sheet(s). Such sheet (s) may closely overlie and extend beyond each material-surrounded wound-fluid NPT drain. Such vapor sealant sheets may feature tube-exit apertures for the vacuum/drainage tube(s) associated with each NPT drain. The perimeter of each vapor sealant sheet associated with an NPT drain may be sealed to the draping layer in an airtight manner and/or to other such perimeter-sealed vapor sealant sheets. Such vapor sealant sheets may be exclusively contacting only other components of the dressing, requiring no contact of the vapor sealant sheets with patient tissue.

5. One or more tube-anchorage and tube-exit-sealant layer(s) associated with the vapor sealant sheet(s) associated with the NPT drain(s). Such layer(s) may mechanically stabilize the placement and orientation within the dressing of the vacuum/drainage tube(s) and of the wound-fluid NPT drain(s). Such layer(s) may seal the tube-exit of the vacuum/drainage tube(s) at and/or along tube-egress from the interior to the exterior of the dressing.

The dressing, basic components and features of which may be summarized above, may be available in several shapes and sizes to accommodate a range of wound types and dimensions. A dressing may contain multiple NPT drains and/or multiple associated vacuum/drainage tubes. Vacuum/drainage tubes of a dressing may be of single-lumen and/or multi-lumen configurations.

The draping layer of the dressing may be configured with areas of wound-facing tissue-adhesive surface alternating (or otherwise mixed) on a given side of the draping layer with areas of non-wound-facing surface: Areas of non-wound-facing surface of the drape may feature full functional sets of the other components as summarized above, coupled with coterminous areas of reverse-side wound-facing tissue adhering surface; each pair of coterminous oppositely sided surfaces may communicate through draping layer perforations as described above.

The draping layer of the dressing may be packaged with a readily removable backing layer protecting and preserving the wound-facing tissue-adhesive surface(s) of the draping layer. A dressing may be provided in appropriately labeled sterile over-wrapping. The wrapped dressing may be supplied in a kit with suitable materials and apparatus for wound-cleansing and debridement and for initial wound-packing.

The dressing that may be described in summary above may streamline and simplify methods for preparation of a wound for NPT. In preparation for application of a dressing to a wound for which NPT is indicated, the wound-site may undergo standard assessment, and irrigation/cleansing of the bed and of the surrounding perilesional area, together with any needed slough-removal/debridement of the wound.

In preparation for application of a dressing, the wound-bed may be slightly under-packed. It should be noted that the wound-bed should not be overpacked. The precaution of slight wound-bed under-packing may accommodate the contraction of the packed wound-bed upon being subjected to negative pressure. The attendant reduction of wound-bed volume may force some of the packing material of a fully packed wound-bed undergoing NPT out onto and/or against the perilesional area, with possible deleterious effects.

The slightly under-packed, almost completely filled wound-bed would not be sealed or draped prior to application of the dressing.

A dressing (of appropriate size, shape and any other characteristics such as, but not limited to, tube lumen configuration and NPT drain number) may be applied directly to the slightly under-packed, almost completely filled wound-bed and to the surrounding wound-site. The following procedural outline is for a representative dressing containing a single drain-associated area of drain-surrounding fluid-absorbing/transferring material(s); adjustments, mainly of repetition, to the following procedural steps may be needed for application of a more complexly configured dressing.)

1. Removing the dressing from its sterile over-wrapping.

2. Removing the backing layer associated with the wound-facing tissue-adhesive surface of the draping layer of the dressing.

3. Orienting the dressing for suitable directionality of its exiting vacuum/drainage tube(s).

4. Approximately centering the drain-surrounding fluid-absorbing/transferring material(s) on the area of the slightly under-packed, almost completely packed wound-bed. Such positioning may yield overlap of the upper surface of the packing material within the wound-bed with the draping layer perforations. The area of drain-surrounding fluid-absorbing/transferring material(s) may be nominally centered within the dressing on the area of the drain layer perforations.

5. Applying the dressing to the wound-site. The tissue-adhesive wound-facing surface of the draping layer should be placed directly over and/or upon the uppermost layer of wound-packing material within the slightly under-packed wound-bed. The dressing should preferably be approximately centered (as described in the previous step) on the wound-bed.

6. Adhering the contour-conforming draping layer of the dressing to the tissue of the surrounding wound-site.

7. Connecting a drain-distal terminus of the vacuum/drainage tube to tubing from a suitable NPT vacuum controller and/or to other treatment control-and-monitor equipment that may be set to enhance NPT wound-healing.

The above-outlined steps involved in preparation of wounds for NPT by means of the dressing may enhance wound-healing using NPT. Further, such a dressing according to the invention may mitigate difficulties, complications and pain associated with preparation of a wound for NPT.

Thus, the dressing provides apparatus that may streamline and simplify methods for readily preparing a wound-site for NPT.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which:

FIG. 1 shows the representative wound at a stage of pre-treatment cleansing prior to wound-packing.

FIG. 2 shows the representative wound with a layer of non-adhering sterile material having been laid upon the base of the wound-bed.

FIG. 3 shows the wound at a typical early stage in conventional procedures for preparation of a wound for NPT, with drain and attached tube in place.

FIG. 4 shows the wound at a subsequent stage of conventional procedures for preparation of a wound for NPT, with wound-packing completed.

FIG. 5 shows the packed wound having been further prepared for NPT by conventional procedures, with the wound and the surrounding wound-site having been covered with an airtight draping material.

FIG. 6 shows the conventionally prepared wound and surrounding wound-site under NPT conditions. The portrayal of the tube-terminus beyond the draping material indicates the functioning of an NPT vacuum controller (not shown).

FIG. 12 shows the representative wound prepared beyond the stage of FIG. 2, having been readied by wound-packing for application of the dressing according to the present invention.

FIG. 13 shows a dressing according to the present invention having been representatively applied to the representative wound and to the surrounding wound-site.

FIG. 14 shows the representative wound (and the surrounding wound-site) and a dressing according to the present invention applied thereto, under NPT conditions.

DETAILED DESCRIPTION OF THE DISCLOSURE

In systems and methods according to the present invention, a dressing may be utilized in preparing a wound for NPT.

The dressing may provide apparatus that may be utilized for preparation of wounds for NPT via a number of steps. By providing apparatus that may reduce the number and complexity of steps involved in wound-preparation for NPT, use of the dressing may streamline and simplify wound preparation for NPT.

Details of systems and methods according to the present invention may be clarified as set forth in the following figures. FIGS. 1-6 portray representative wounds either alone or in association with representative NPT dressings in various stages of conventional preparation or use. FIGS. 7-14 portray representative dressings according to the present invention, either alone or in association with wounds.

Figure 1:
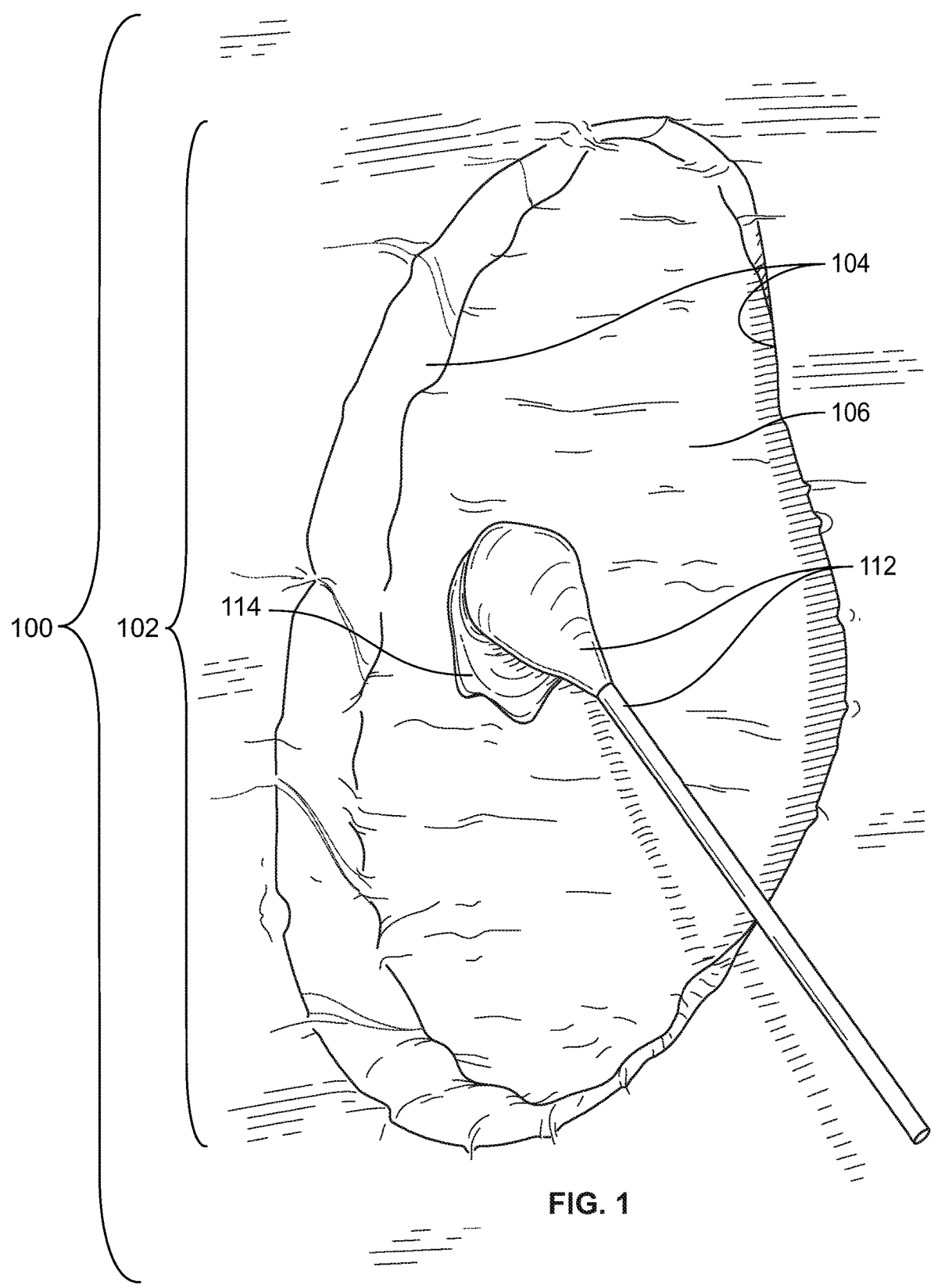
FIGS. 1-6 show a representative wound typical of wounds for which NPT may be clinically indicated.

FIG. 1 is a perspective view of a representative wound. The wounds represented may be surgical or traumatic wounds, acute or chronic wounds, or other wounds, including but not limited to wounds produced by surgical excision, specific degloving injuries, particular burns, diabetic extremity ulcers, and pressure sores. Such wounds may be on and/or in non-human surfaces. All such wounds are considered for application of the dressing according to the present invention.

The representative wound of FIG. 1 is portrayed as a wound-bed 102 surrounded proximally by an area 100 of perilesional tissue. Considering FIG. 1 as a flat horizontal field, the portrayal is seen by a viewer stationed beyond the field's "FIG." number-bearing edge, that edge of the figure being the edge closest to the viewer. The viewer is taken as facing in the direction of area 100, lined up approximately with the "FIG." number, and peering down at wound-bed 102 from directly above. In the rendering of FIG. 1, overhead illumination is taken as being incident upon area 100 and wound-bed 102 from the viewer's right. In this application, wound-figure illustrations and perspective-view illustrations of the present invention may utilize this perspective view.

The terms "right" and "left" as used herein for orientation and to distinguish aspects of designated illustrated features, refer to the right and left, respectively, of the above described viewer. Likewise, the terms "near" and "far" as used herein to distinguish aspects of designated illustrated features, refer to those aspects' relative closeness to the viewer's station beyond the "FIG." number-bearing near edge of each figure. The terms "below" (or "beneath") and "above" as used herein to distinguish aspects of designated illustrated features associated with the wound-bed and/or the wound-dressing, refer to those aspects' being, respectively, vertically proximal to and vertically distant from the wound-base, as per the perspective view utilized and along the line-of-sight of the viewer, along which a displacement from "below" to "above" would be toward the viewer. Likewise, the terms "lower" (or "down" or "downward") and "upper" (or "up" or "upward") as used herein to distinguish aspects of designated illustrated features associated with the wound-bed and/or the wound-dressing, refer to those aspects' being, respectively, vertically proximal to and vertically distant from the wound-base, as defined for "below" and "above."

In FIG. 1, wound-bed 102 features a base 106 surrounded and defined by a set of walls 104. The portrayal of wound-base 106 and wound-walls 104 features texturing typical of exposed subcutaneous tissue. Such choice of tissue and its associated texturing are representative and not limiting; any wound surfaces for which NPT may be clinically indicated are considered.

In FIG. 1, wound-base 106 is lower than the perilesional skin of proximal area 100 by the depth of wound-walls 104.

FIG. 1 shows wound-bed 102 at a representative stage of pre-treatment cleansing prior to wound-packing. The representative cleansing of wound-bed 102 in FIG. 1 portrays an area of wound-base 106 having a medicinal salve (or cleansing agent) 114 being applied to it by means of a stick-and-swab 112. Pre-treatment methods may be utilized in various combinations to achieve the desired preparation of wound-bed 102. Pre-treatment cleansing may typically involve all surfaces of wound-bed 102. Area 100 may also be suitably cleansed in preparation for wound treatment.

Figure 2:
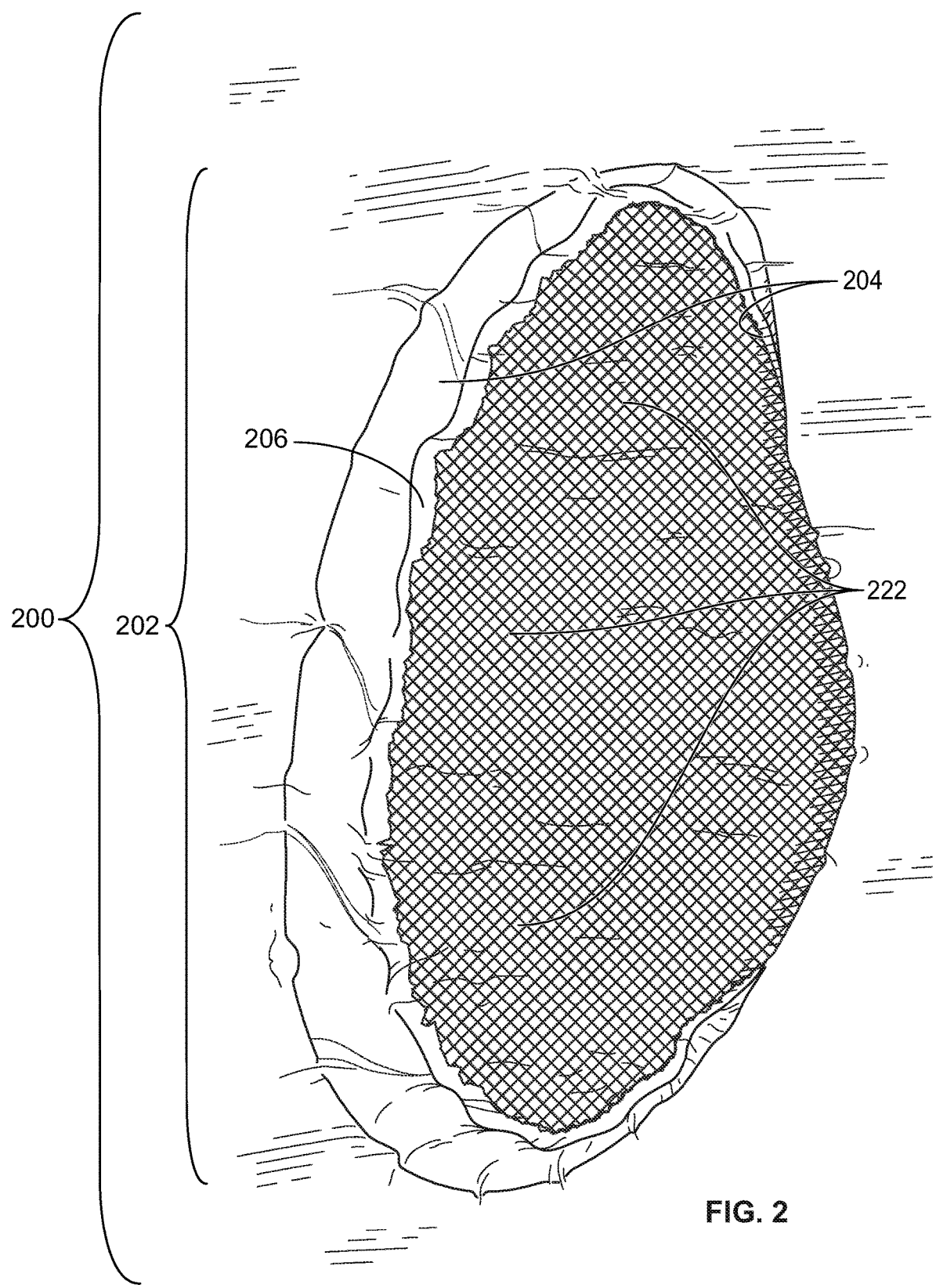

FIG. 2 is a perspective view showing the representative wound subsequent to the pre-treatment procedures representatively portrayed in FIG. 1. In FIG. 2, perilesional area 200 and wound-bed 202 may have been prepared for wound-packing by appropriate pre-treatment procedures. Typically, the wound-bed is clinically assessed before being packed. Preparatory to the scene portrayed in FIG. 2, an initial layer of dressing material may have been shaped (typically, cut) to closely match the contours of wound-base 106 of FIG. 1. Usually, the shaped material may have been prepared slightly undersized relative to wound-base 106, allowing for ease of placement within the wound-bed and for anticipated subsequent reduction of wound-base area through healing. The dressing material may typically have been treated, possibly during manufacture, to be non-adhering to wound surfaces and to have other clinically appropriate characteristics.

FIG. 2 shows gauze 222 having been laid down across much of the wound-base. Gauze 222 is representative of a wound-shaped, slightly under-sized, non-adhering initial dressing material laid into wound-bed 202 prior to wound-packing. Gauze 222 is representative of any such suitable material, including but not limited to knitted fabrics such as Smith and Nephew's ADAPTIC™ dressing and non-woven polymer surfaces such as Boehringer's BIO-DOME™ dressing.

In FIG. 2, gauze 222 is portrayed as having been inserted within wound-bed 202, laying upon and across the wound-base with some clearance from wound-walls 204 roundabout the wound-base. Exemplary non-covered wound-base 206 is shown proximal to the left wound-wall 204.

Figure 3:
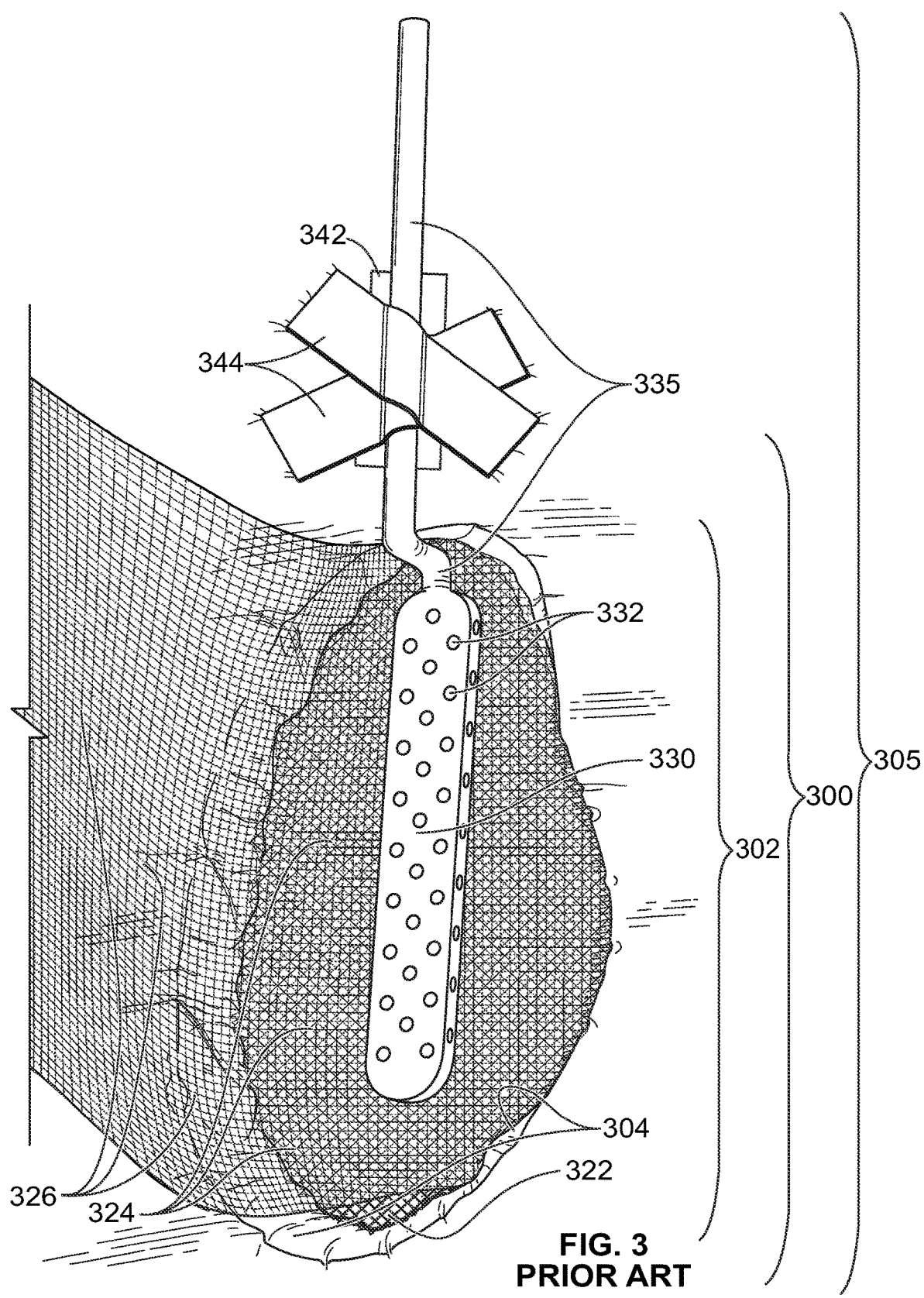

FIG. 3 is a perspective view of a typical early stage in conventional procedures for preparation of a wound for NPT. On top of non-adhering initial dressing 322, a wound-packing material 324 is shown in wound-bed 302. To the left of wound-bed 302, exiting packing material 324 is shown as continuous with a supplementary section of packing material 326, perspectively portrayed as suspended above the left side of area 300.

In FIG. 3, packing materials 324 and 326 are portrayed as gauze. Alternate conventional procedures of wound-packing preparation for NPT may utilize other varieties of packing material such as various shapeable sponge-like foams, such as V.A.C.® GRANUFOAM™.

FIG. 3 portrays an early stage in conventional procedures for preparation of a wound. A representative conventional NPT drain 330 is shown having been emplaced upon the early layering of packing material 324 within wound-bed 302. NPT drain 330 typically features a hollow interior surrounded by walls transversely perforated by one or more holes represented by a set of NPT drain holes 332. Holes 332 provide access from outside NPT drain 330 to the hollow core of NPT drain 330. NPT drain 330 may be any suitable shape—e.g., cylindrical, flat, flattened cylindrical, etc.

In FIG. 3, the near terminus of a vacuum/drainage tube 335 is shown associated with and exiting from NPT drain 330, the hollow core of tube 335 understood to be continuous with the hollow core of drain 330. Tube 335 is shown extending from area 300 to a region of a wider wound-site 305 where the far tube-terminus is portrayed as located.

In FIG. 3, NPT drain 330 is representatively portrayed oriented with vacuum/drainage tube 335 exiting up out of wound-bed 302 at far wound-wall 304 to lie along far perilesional area 300.

The location and orientation of drain 330 within wound-bed 302 may impact the effectiveness of NPT. Any of holes 332 being highly proximal to a section of wound-walls 304 may, under the negative pressure conditions of NPT within wound-bed 302, damage tissue of wound-walls 304. Drain 330 drawing exudate preferentially from one side of the wound-bed may thwart promotion of symmetric wound-healing. These and similar considerations underscore the need for fixity of NPT drain location and orientation after emplacement by practitioner-manipulation. Ideally, drain 330 would be fixed in location and orientation by some apparatus directly within the defined borders of wound-bed 302. In conventional wound-preparation procedures for NPT, such apparatus-placement within wound-bed 302 may, however, interfere with subsequent wound-packing, exudate-drainage and/or wound-healing.

As shown in FIG. 3, anchoring drainage/vacuum tube 335 to the patient's skin may be the approach used to maintain the location and orientation of NPT drain 330 relative to wound-bed 302. While high proximity of tube-anchorage to wound-bed 302 may improve drain-fixity, perilesional skin of area 300 proximal to wound-bed 302 may be too frail or sensitive to serve as a tube-anchorage site. In addition, the usual apparatus for tube-anchorage, a set of skin-adhesive (and, possibly, tube-adhesive) strips 344, typically tape, but which may also be formed from another suitable sealant such as pliable putty, may interfere with perilesional participation in wound-healing. As presented, adhesive strips 344 anchor vacuum/drainage tube 335 onto the patient's skin at a far region of perilesional area 300 that is part of a region of wider wound-site 305. A layer of skin-protective material 342, such as pliable putty, laid down upon the patient's skin prior to laying tube 335 across it, is shown running under the section of tube 335 below the set of adhesive strips 344. Layer 342 and adhesive strips 344 shown are representative of a range of suitable materials including skin-adhesive ostomy strips and surgical tape.

Even with anchorage of tube 335 in proximity to wound-bed 302, the location and orientation of NPT drain 330 relative to wound-bed 302 may be subject to shifting. Such shifting may result from practitioner-manipulations involved in subsequent steps of conventional procedures for wound-preparation for NPT. Even in circumstances that allow for correction of such shifting within conventional procedures for wound-preparation for NPT, sub-optimality of care may result. Such corrections may involve adjustment or replacement of components of dressing, drain and/or anchorage, which may contribute to patient discomfort.

Figure 4:
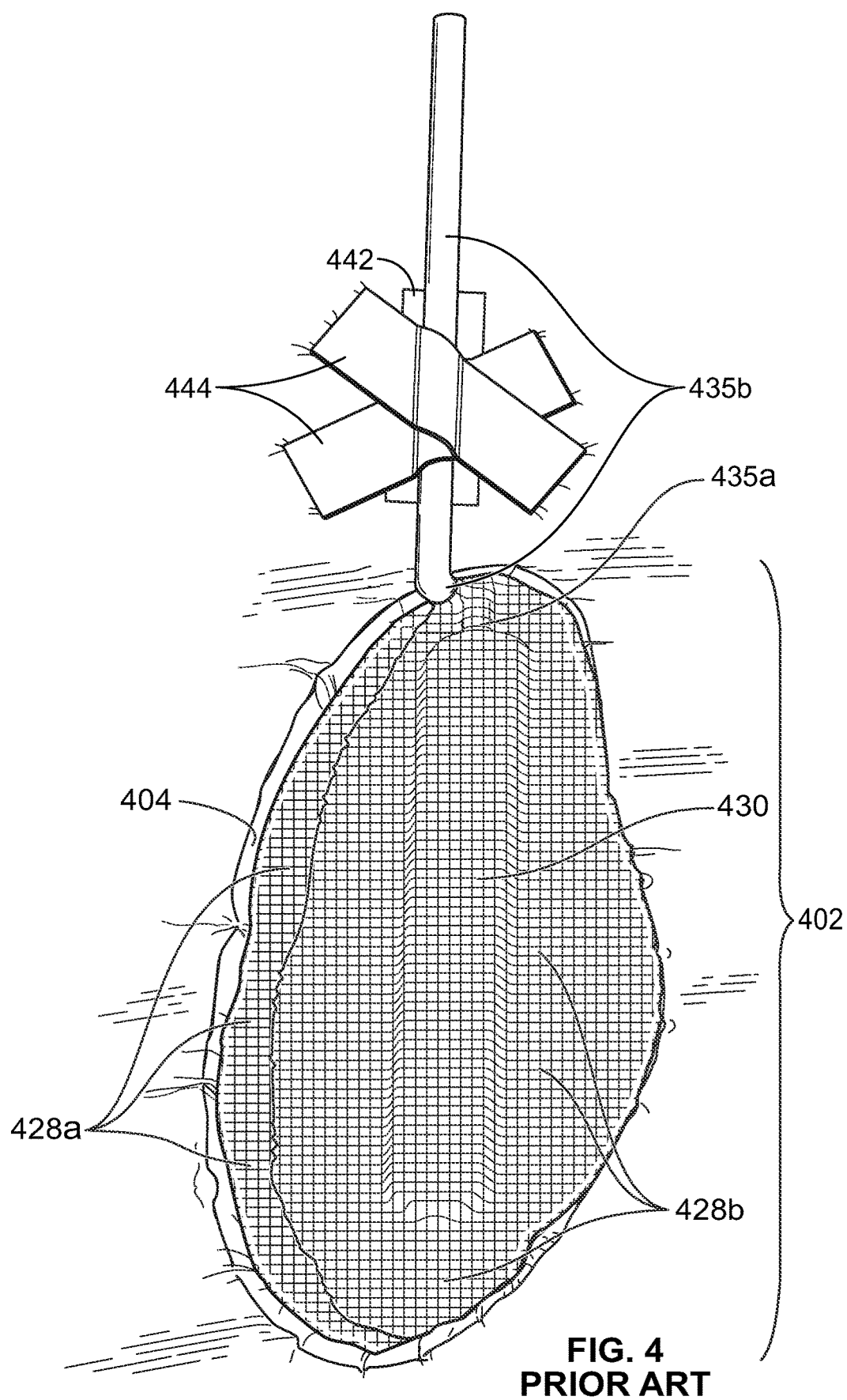

FIG. 4 is a perspective view of a typical stage in conventional procedures for preparation of a wound for NPT, subsequent to wound-bed packing and preparatory to wound-site draping. In FIG. 4's portrayal of almost fully packed wound-bed 402, material 428b is representative of an uppermost layer of packing material; material 428a is representative of lower layers of packing material.

In FIG. 4's portrayal of almost completely packed representative wound-bed 402 prior to draping, NPT drain 430 within wound-bed 402 is directly indicated as covered by packing material 428b; below layer 428b, NPT drain 430 may be covered by layers 428a. Proximal to the far end of covered NPT drain 430, a section of vacuum/drainage tube 435a associated with the drain is indicated as covered by material 428a-b. A near section of vacuum/drainage tube 435b, continuous with the gauze-covered tube section 435a, is portrayed exiting from packing material 428a-b in the vicinity of far wound-wall 404. The near section of vacuum/drainage tube 435b is portrayed as completing its climb up and out of wound-bed 402 in the vicinity of far wound-wall 404, to lie upon the surrounding perilesional area (as depicted in FIG. 3 for vacuum/drainage tube 335 exiting wound-bed 302 to lie upon area 300). Wound-site skin-anchorage of tube-section 435b via skin-adhesive strips 444, typically tape, but which may also be formed from another suitable sealant such as pliable putty, and skin-protective material 442 is as described in FIG. 3 for strips 344 and material 342, respectively.

Figure 5:
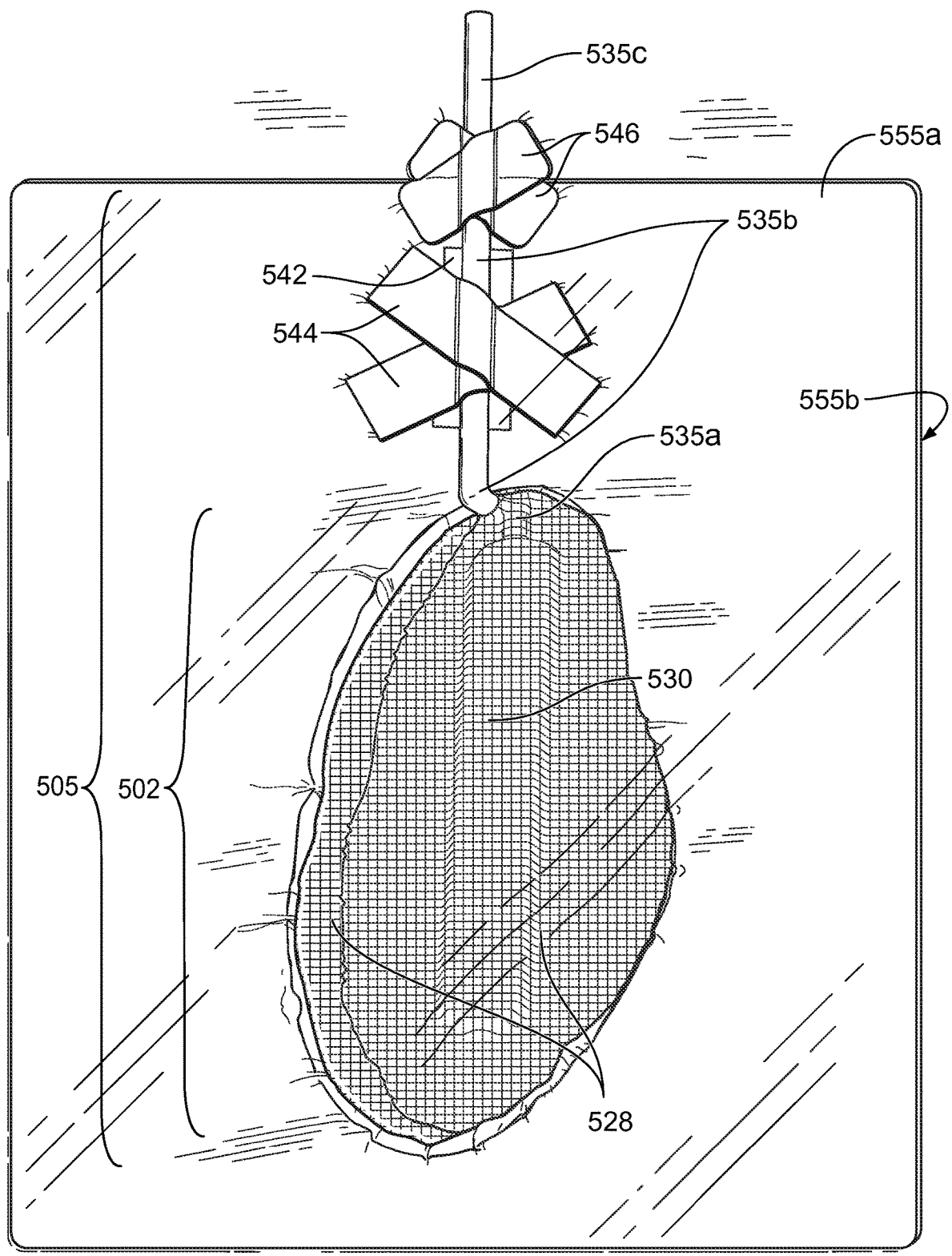

FIG. 5 is a perspective view of a typical stage in conventional procedures for preparation of a wound for NPT. The stage portrayed may be subsequent to wound-bed draping and preparatory to reduction of wound-bed ambient air pressure by use of an NPT vacuum controller. The wider wound-site 505, inclusive of wound-bed 502 and its associated perilesional area, is shown as having been draped with a representative contour-conforming material 555a-b. The lower surface of draping material 555a-b, designated 555b, may typically be skin-adhesive. Draping material 555a-b may typically be flexible, facilitating close conforming of 555a-b to the underlying contours of site 505.

Draping material 555a-b portrayed in FIG. 5 is typically impermeable to liquids and gases. By conventional practice, practitioner-smoothing of skin-adhesive material 555a-b to conform to site 505 contouring, may effect an airtight perimeter seal between surface 555b and the patient's skin across draped surfaces of site 505 roundabout wound-bed 502.

Draping material 555a-b may be transparent, as portrayed in FIG. 5. Visible beneath draping material 555a-b, wound-bed 502 is portrayed with drain 530 and its associated section of vacuum/drainage tube 535a indicated as present beneath layers of packing material 528. The section of vacuum/drainage tube 535b running from the wound-bed across the patient's skin of wider wound-site 505 is portrayed beneath draping material 555a-b. Wound-site skin-anchorage of tube-section 535b via skin-adhesive strips 544 and skin-protective material 542 is as described in FIG. 3 for strips 344 and material 342, respectively. The egress of the section of vacuum/drainage tube 535c from the perimeter of the drape is shown as having been sealed by an adhesive material 546, typically tape.

Figure 6:
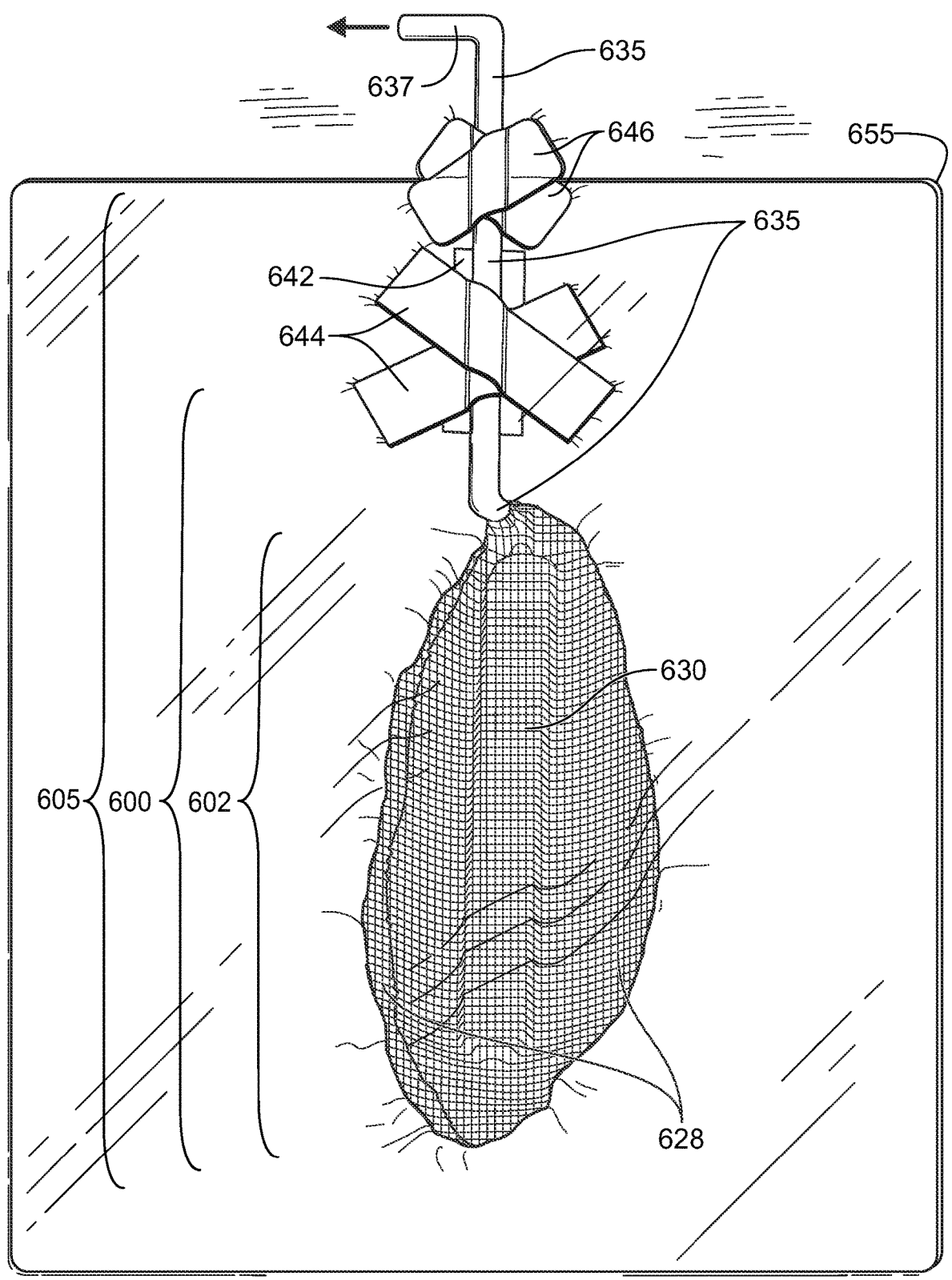

FIG. 6 is a perspective view of a conventionally prepared representative wound-site 605 under NPT conditions. Beneath contour-conforming draping material 655, wound-site skin-anchorage of tube 635 via skin-adhesive strips 644 and skin-protective material 642 is portrayed as described in FIG. 3 for strips 344 and material 342, respectively; airtight sealing via adhesive material 646 of the tube-egress from drape 655 is portrayed as described for adhesive material 546 of FIG. 5. In FIG. 6, the terminus of tube 635 shown beyond drape 655, is designated 637, and displays an outward-directed arrow.

FIG. 6 portrays conventionally prepared wound-site 605 under NPT conditions of partial vacuum within wound-bed 602. Those conditions are produced by the NPT vacuum controller acting through tube-terminus 637 upon suitably prepared wound-bed 602 and wound-site 605. In FIG. 6, wound-bed 602 is portrayed as contracted, smaller than the same-scale portrayal of wound-bed 502 of FIG. 5. Perilesional area 600 proximal to wound bed 602 is portray distorted, its edge is drawn inward toward the contracted wound-bed.

In FIG. 6, draping material 655 above packed wound-bed 602 is shown pulled downward into the wound-bed, pressed against packing material 628; packing material 628 is shown distorted (relative to the portrayal of packing material 528 of FIG. 5), compressed within the vacuum-reduced volume of wound-bed 602.

Under NPT conditions portrayed in FIG. 6, exudate would be drawn from the wound-base and wound-walls through packing material 628 to NPT drain 630 and out through vacuum/drainage tube 635 toward the NPT vacuum controller.

Pressure-settings and time-duration of NPT treatment (including use of ON/OFF cycling to produce intermittent NPT within a course of treatment) may vary as functions of several parameters. Such parameters may include wound-type, accepted institutional procedures, wound-packing material, vacuum controller, and practitioner training and predilections.

The apparatus of the present invention preferably reduces time and increases efficiency of implementation of NPT. Specifically, certain embodiments of the invention provide a first dressing layer and a second dressing layer. These two layers may preferably trap one or more layers of fluid-absorbing/transferring material in between the two dressing layers.

In one of the layers, perforations may exist that roughly correspond to the location of the fluid-absorbing/transferring material within the layers. A drain for removing fluid may be located in between the fluid-absorbing/transferring material layers, or proximal a single fluid-absorbing/transferring material layer.

In the other dressing layer, an aperture may exist that allows a drainage tube to pass through the other dressing layer. The tube connects to the wound-fluid drain. The structure of such a dressing may preferably promote efficient implementation of NPT on a wound at least because it allows the dressing to be more easily, and more quickly, applied to a patient.

Alternative embodiments of the dressing may include a single perforation in one of the dressing layers and the perimeter of the fluid-absorbing/transferring material affixed to the edges of the perforation. The structure of such an embodiment may also promote efficient NPT on a wound. Specifically, such a structure may promote efficient NPT at least because the structure can be applied in fewer steps than a conventional dressing which, typically, requires application in a component-by-component fashion.

Alternatively, one or more layers of the fluid-absorbing/transferring material may only be fixed to the dressing layer that does not include the perforation. In yet other embodiments, the fluid-absorbing/transferring material may be adhered both to the edges of the perforation and to the dressing layer that does not include the perforation.

FIGS. 7-13 are views of embodiments of a dressing according to the present invention. The dressing according to the present invention, components and functionality of which may be portrayed in FIGS. 7-13, may be available in several shapes and sizes to accommodate a range of wound types and dimensions; the embodiments in FIGS. 7-13 are representative.

The dressing may be provided in an appropriately labeled sterile over-wrapping. Such over-wrapping may be provided for shipping, storage, protection and/or maintenance of sterile conditions. Such over-wrapping may indicate various characteristics of the components of the over-wrapped dressing as may be useful in selecting a particular dressing for matching to a given wound-type on or in a given wound-site. Additionally, the wrapped or unwrapped dressing may be supplied in (association with) a kit with suitable materials and apparatus for wound-cleansing and debridement and for initial wound-packing. The outer packaging of such kit may provide identification of contents of the kit, including those characteristics of the dressing that may be useful in selecting for matching of dressing to wound. The embodiments of the dressing according to the present invention in FIGS. 7-13 are shown independent of any such kit and without any over-wrap.

Figure 7A:
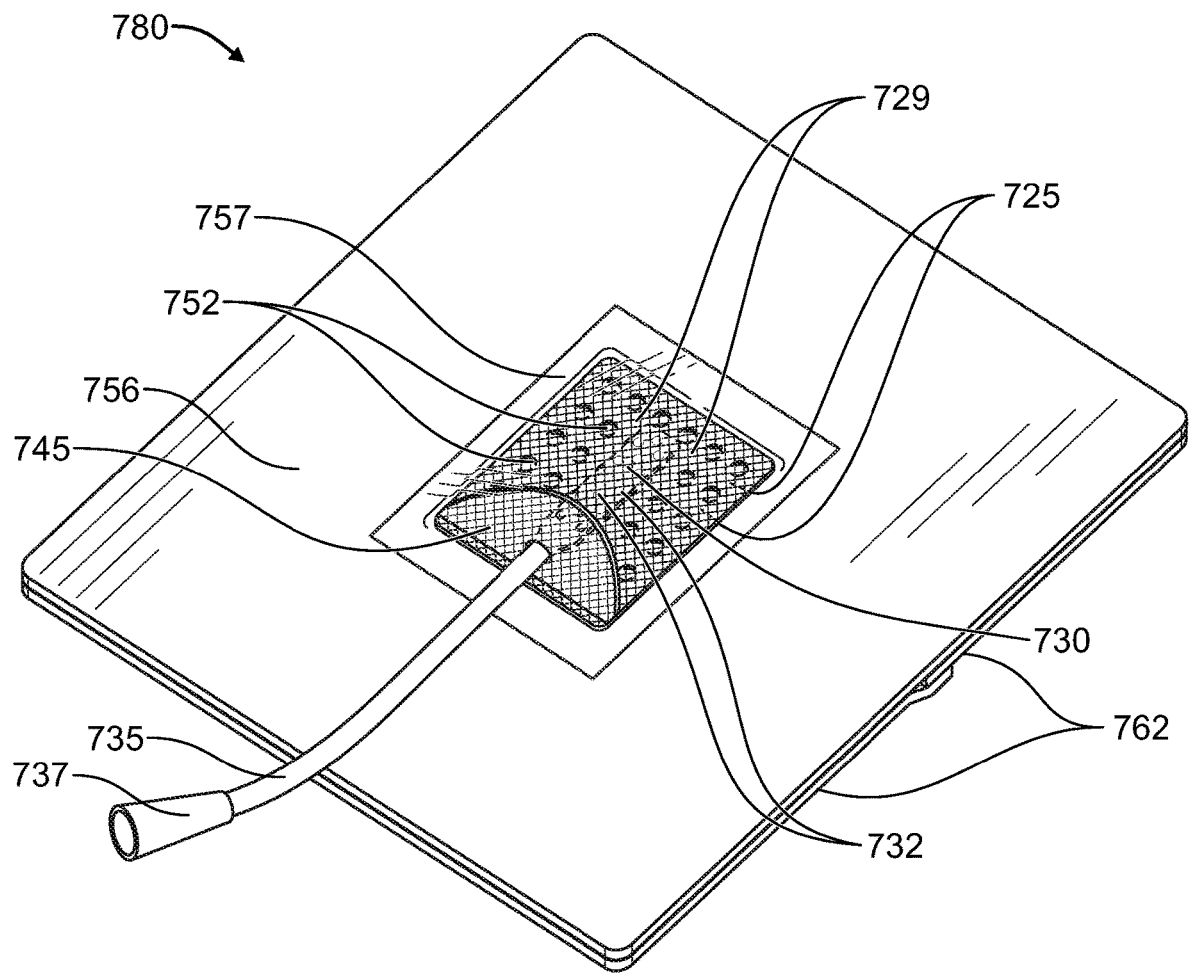
FIGS. 7A-C show views from "above" of embodiments of a dressing according to the present invention.
Figure 7B:
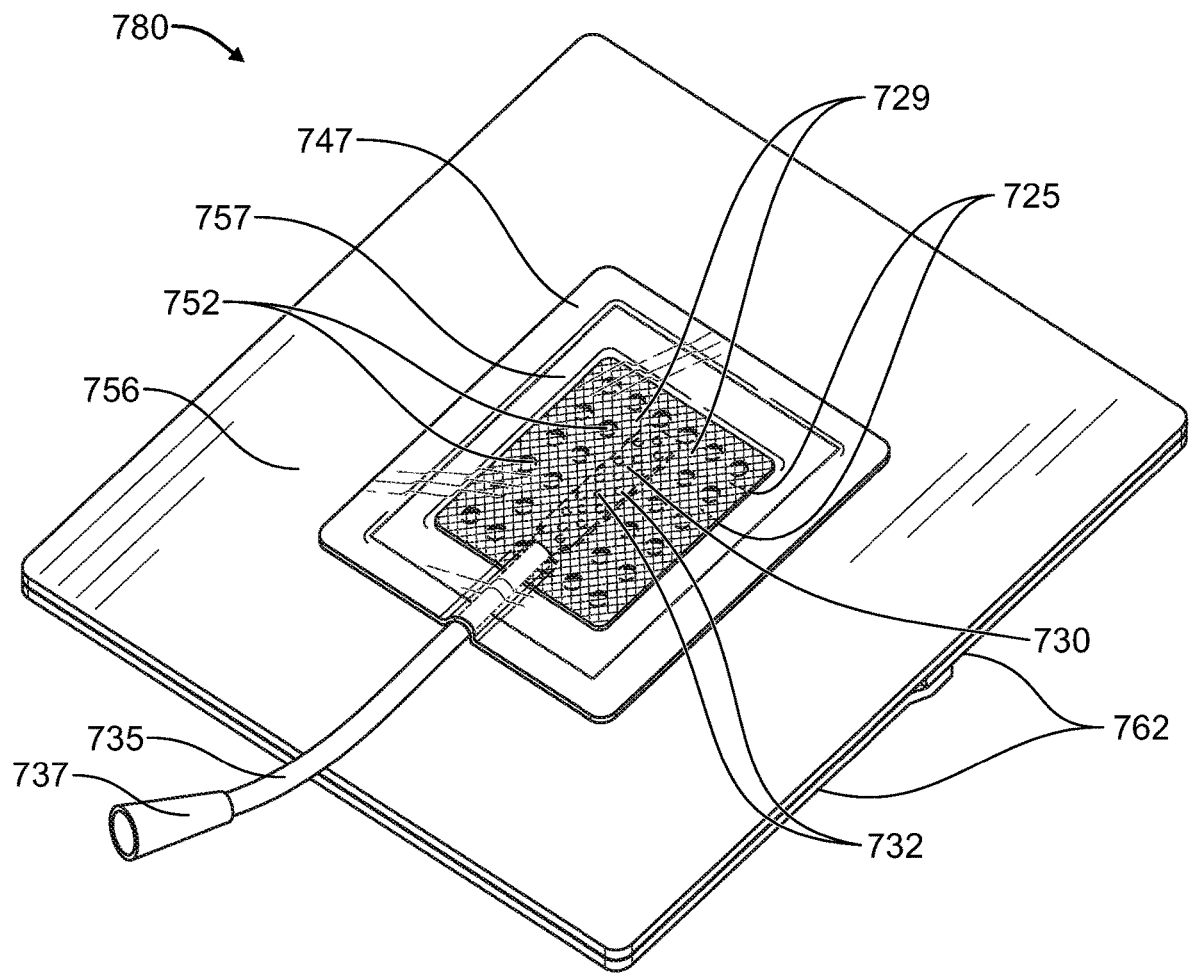
Figure 7C:
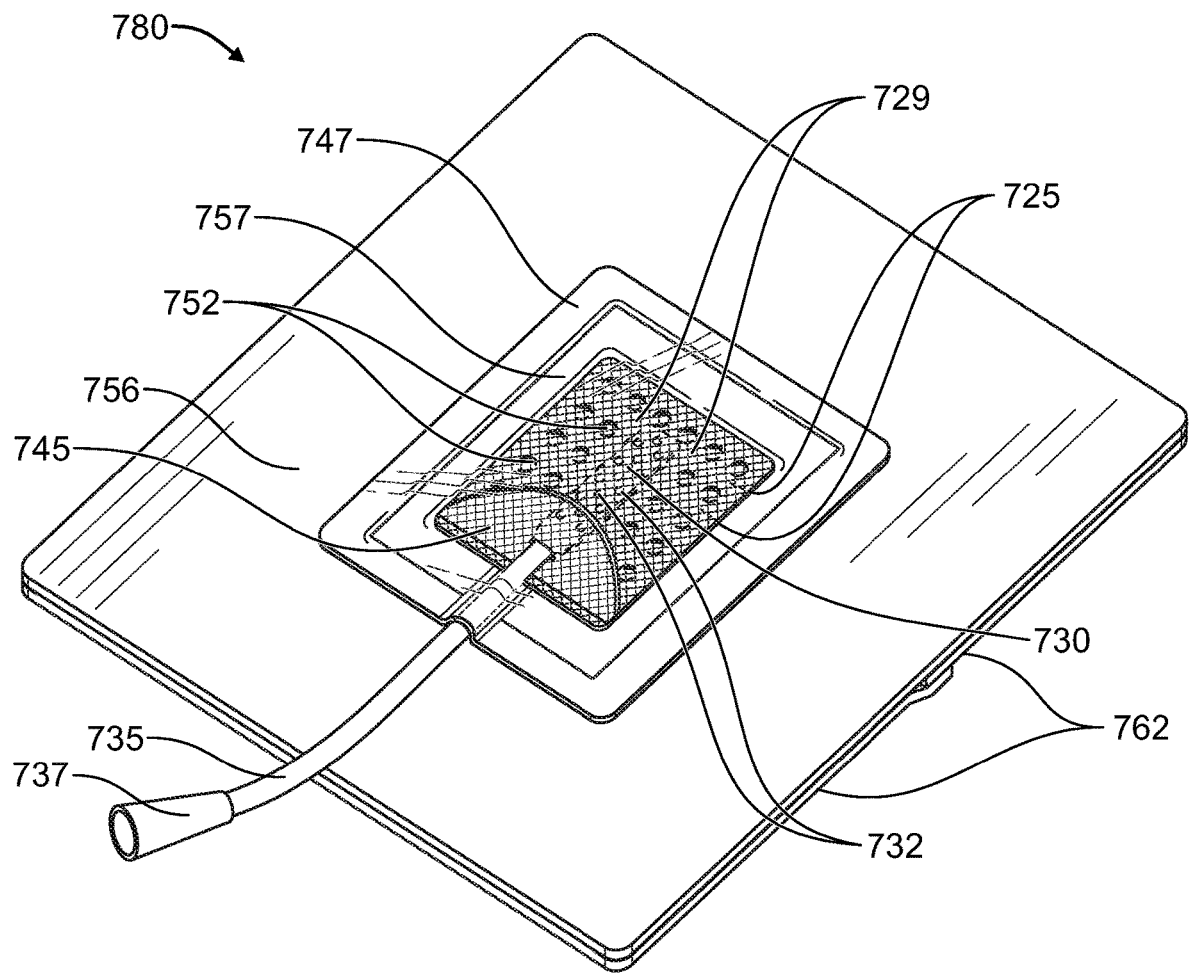

FIGS. 7A-C are perspective views from above of embodiments of a dressing 780 according to the present invention. Perspective views of the dressing in this application maintain the linked set of view, orientation and directionality utilized for portrayal of wounds in FIGS. 1-6.

In FIGS. 7A-C, dressing 780 may also incorporate components not typically assembled in conventional NPT wound-preparation procedures. Components of dressing 780 may be suitably rated and/or approved for their use in patient care and/or for their use under NPT conditions of low air pressure.

FIGS. 7A-C representatively present the components of dressing 780 according to the present invention. As portrayed in FIGS. 7A-C, these components may include (with select components specifically presented in only two of the three FIGS. 7A, 7B and 7C, to be specified below as such):

1. A wound-fluid NPT drain 730. Wound-fluid NPT drain 730 of dressing 780 according to the present invention may be a hollow tube-like structure featuring transversely perforated walls, the perforations represented by a set of holes 732. Holes 732 represent one or more transverse perforations that may provide access, possibly through a wall of drain 730, to the hollow core of drain 730. Such perforations 732 may be of a range of suitable sizes and shapes, and may be variously and selectively located along the wall(s) of drain 730. Drain perforations 732 may be or may include the open terminus of a tube-like drain. In certain embodiments, drain 730 may be shaped as a flattened tube or in any other suitable configuration that allows for draining exudates.

Drain 730 of dressing 780 according to the present invention may be flexible and may be of a variety of materials, shapes, sizes and configurations. Drain 730 may be as structurally straightforward as a section of tube featuring a single hole 732; drain 730 may be as structurally complex as a multi-part, multi-functional manifold featuring multiple, uniquely shaped and spaced holes 732, and featuring flow-control modalities (e.g., anti-clogging), sensing capabilities (e.g., pressure-monitoring), signaling functions (e.g., indication of dressing-change time), and/or anti-bacterial or anti-microbial properties.

A dressing 780 according to the present invention may feature more than one wound-fluid NPT drain; each may be described as presented above in the description of wound-fluid NPT drain 730. The location and orientation of each NPT drain 730 within a dressing 780 may be indicated on the dressing (and on and/or through any packaging over-wrapping of the dressing).

2. A vacuum/drainage tube 735. Vacuum/drainage tube 735 of dressing 780 according to the present invention may provide a conduit through which low air pressure may be applied (via drain 730) to a wound-bed and through which wound-fluid exudate may be drawn (via drain 730) from a wound-bed. One terminus of vacuum/drainage tube 735 may be associated with NPT drain 730. The association of tube 735 with drain 730 may be by structural attachment to drain 730. The hollow core of tube 735 may be continuous with the hollow core of drain 730. The hollow core of drain 730 may or may not be capped on the end of drain 730 opposite its juncture of continuity with tube 735.

Vacuum/drainage tube 735 of dressing 780 according to the present invention may be available in a variety of materials (such as silicon tubing, plastic tubing or other suitable tubing material), strengths, flexibilities, lengths and carrying capacities. Vacuum/drainage tube 735 of dressing 780 may feature a single lumen of a range of cross-sections or a multiple set of lumens of various ranges of cross-section. Multi-lumen vacuum/drainage tube 735 may be of various configurations including, but not limited to, coaxial lumens and side-by-side lumens. Multi-lumen vacuum/drainage tube 735 may be configured at tube-termini with unique connectors and connections for specific sets of lumens or for each lumen, facilitating multiple uses of tube 735.

Non-standard uses of vacuum/drainage tube 735 may be facilitated by the availability of multiple lumens. Such uses may or may not be carried out simultaneously with the standard use of at least one lumen of tube 735 for application of negative pressure to a wound-bed and for exudate-drainage from the wound-bed. Such multi-lumen uses include, but are not limited to, measurement via a lumen of ambient pressure within a wound-bed; flushing via a lumen of clogged drain holes 732; delivery via a lumen of medicinal fluids to a wound-bed as part of a course of treatment; delivery via a lumen of apparatus or agents capable of providing information relative to ambient conditions, such as temperature, within the wound-bed; access via a lumen to a wound-bed by catheter-borne equipment of diagnostic, therapeutic and/or interventional utility; and delivery via a lumen of flushes of surfactant, cleansing and/or irrigating fluids to a wound-site preparatory to wound-dressing changes.

In dressing 780 according to the present invention, the terminus of tube 735 distal to drain 730 may feature a tube-connector adapter 737 that may be available in a variety of sizes and configurations. Adapter 737 may facilitate airtight connection to tubing leading to an NPT vacuum controller as well as connection to other treatment control-and-monitor equipment. Tube-terminus adapter 737 is representative of single and multiple tube-terminus adapters. For a multi-lumen tube 735, a set of one or more adapters 737 may terminate the drain-distal end of tube 735, each adapter of the set containing the connection(s) needed for one or more lumens connected to it and each adapter of the set possibly uniquely oriented as per its associated lumen(s).

A dressing 780 according to the present invention may feature more than one vacuum/drainage tube; each may be described as presented above in the description of vacuum/drainage tube 735. Each such vacuum/drainage tube may be associated with one or more NPT drains; each of the latter may be described as presented above in the description of wound-fluid NPT drain 780.

3. A set of layering of fluid-absorbing/transferring materials 725 and 729, which may surround drain 730, enfolding the drain between a lower layer 725 and an upper layer 729. As portrayed, fluid-absorbing/transferring layers 725 and 729 may be nominally centered within the larger overall area of dressing 780 according to the present invention; drain 730 may be nominally centered on the area of layers 725 and 729, from which vacuum/drainage tube 735 may exit. Such portrayed centering is representative and not limiting; the location of drain 730 relative to layers 725 and 729 and of layers 725 and 729 relative to the larger overall area of dressing 780 may be varied to accommodate different shapes and configurations of the dressing.

Fluid-absorbing/transferring layers 725 and 729 of dressing 780 according to the present invention may feature a variety of shapes, areas and thicknesses. Different shapes and configurations of the dressing featuring variously configured fluid-absorbing/transferring layers 725 and 729 associated with variously configured NPT drains 730, may be optimized for wounds of different types, sizes and/or shapes. Layers 725 and 729 of dressing 780 may be flexible and may be comprised of gauze or other suitable materials. Layer 725 and layer 729 may differ from each other as to compositional materials and as to characteristic shapes, areas and thicknesses. Layers 725 and 729 may be of materials different from that of the packing within the wound-bed. For materials such as foam, layers 725 and 729 may represent the lower and upper segments, respectively, of such materials in which drain 730 is located. Layers 725 and 729 may or may not bear antimicrobial, bacteriostatic, surfactant, cleansing or ameliorative medicinal agents.

Fluid-absorbing/transferring layers 725 and 729 of dressing 780 are representative of one or more sets of such materials, each set containing one or more drains 730 each featuring one or more exiting tubes 735; the dressing according to the present invention may incorporate multiple drains 730 associated with layers 725 and 729. Layers 725 and 729 may or may not be structurally integral to drain 730. The dressing according to the present invention may feature a drain 730 comprised of and built into suitable material layers 725 and 729; the dressing according to the present invention may feature layers 725 and 729 configured from and linked to the material of drain 730.

A dressing 780 according to the present invention may feature multiple sets of fluid-absorbing/transferring layers 725 and 729. Such sets may differ from each other with respect to characteristic shape, area, thickness, orientation and/or compositional material(s), as well as with respect to the number and characteristics of the NPT drains surrounded and/or enfolded thereby and/or comprised thereof.

4. A contour-conforming draping layer 756. Contour-conforming draping layer 756 of dressing 780 according to the present invention may serve as draping material for a wound-bed. Contour-conforming draping layer 756 may be transparent or translucent, with such transparency/translucency useful in positioning dressing 780 relative to a wound-bed to which it may be applied and, after application of dressing 780, in visually monitoring the condition of said wound-bed during a course of NPT. Contour-conforming draping layer 756 may be comprised of one or more materials that confer flexibility and airtightness on draping layer 756; draping layer 756 may be comprised of one or more materials that confer on a surface of the drape the capability of adhering even to moist, contoured surfaces of a patient's body, generally to perilesional skin and other wider wound-site skin. Such transparent/translucent, airtight, flexible, contour-conforming, tissue-adhering materials may include, but are not limited to, such hydrocolloids as ER Squibb's Duoderm® and 3M's Tegaderm™ or any other suitable hydrocolloid material or other suitable material. The composition and geometry of draping layer 756 may allow for repeated applications to and smoothing manipulations upon patient body surfaces, resulting in NPT-suitable tissue-adhesion and airtightness, even on moist contoured surfaces. Such airtight, flexible, contour-conforming, tissue-adhering draping layer 756 may be of suitable composition and geometry to maintain such characteristics under NPT conditions.

Figure 9:
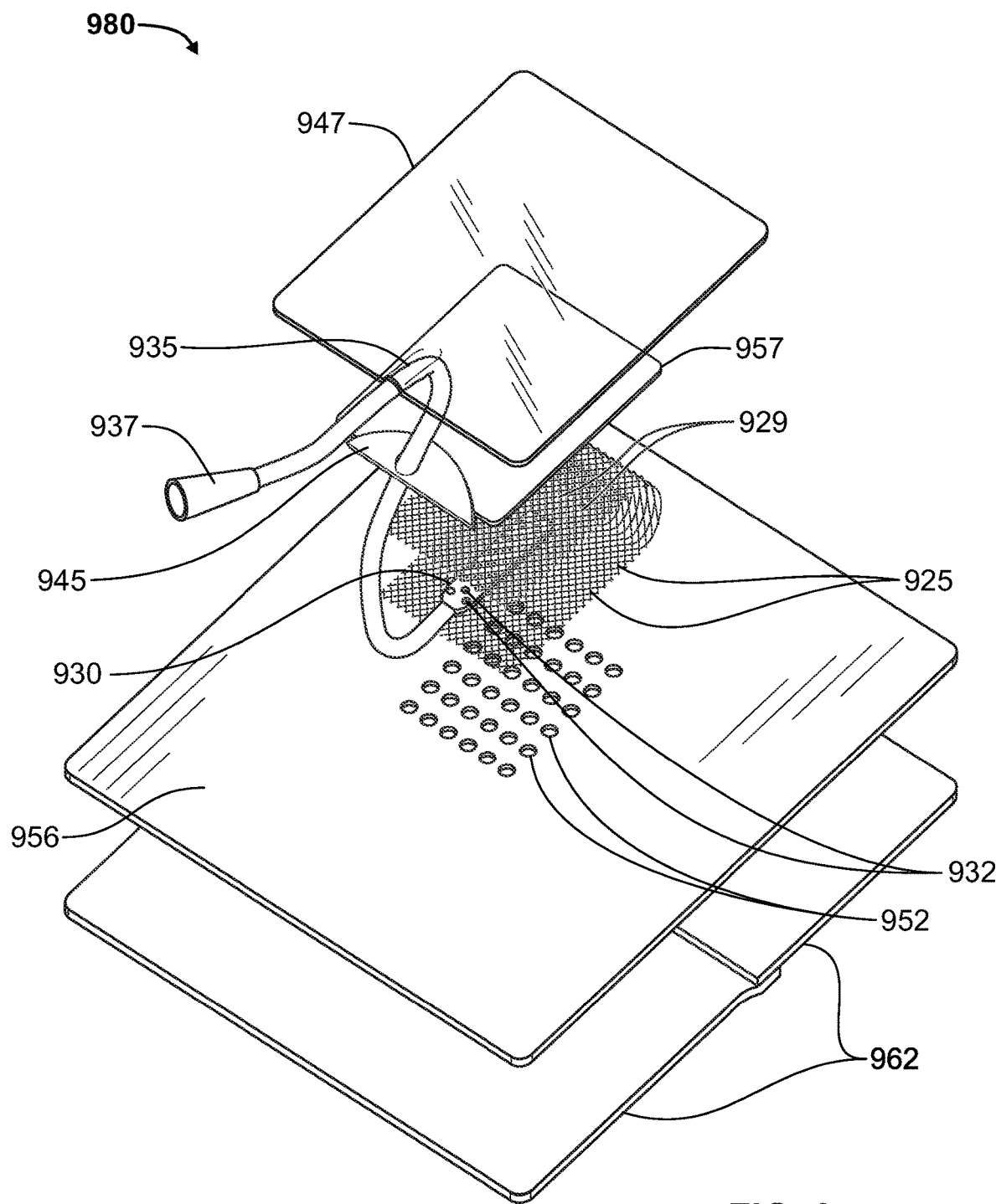
FIG. 9 shows an exploded, multi-tiered view from "above" of layers of components of an embodiment of the dressing according to the present invention.
Figure 10:
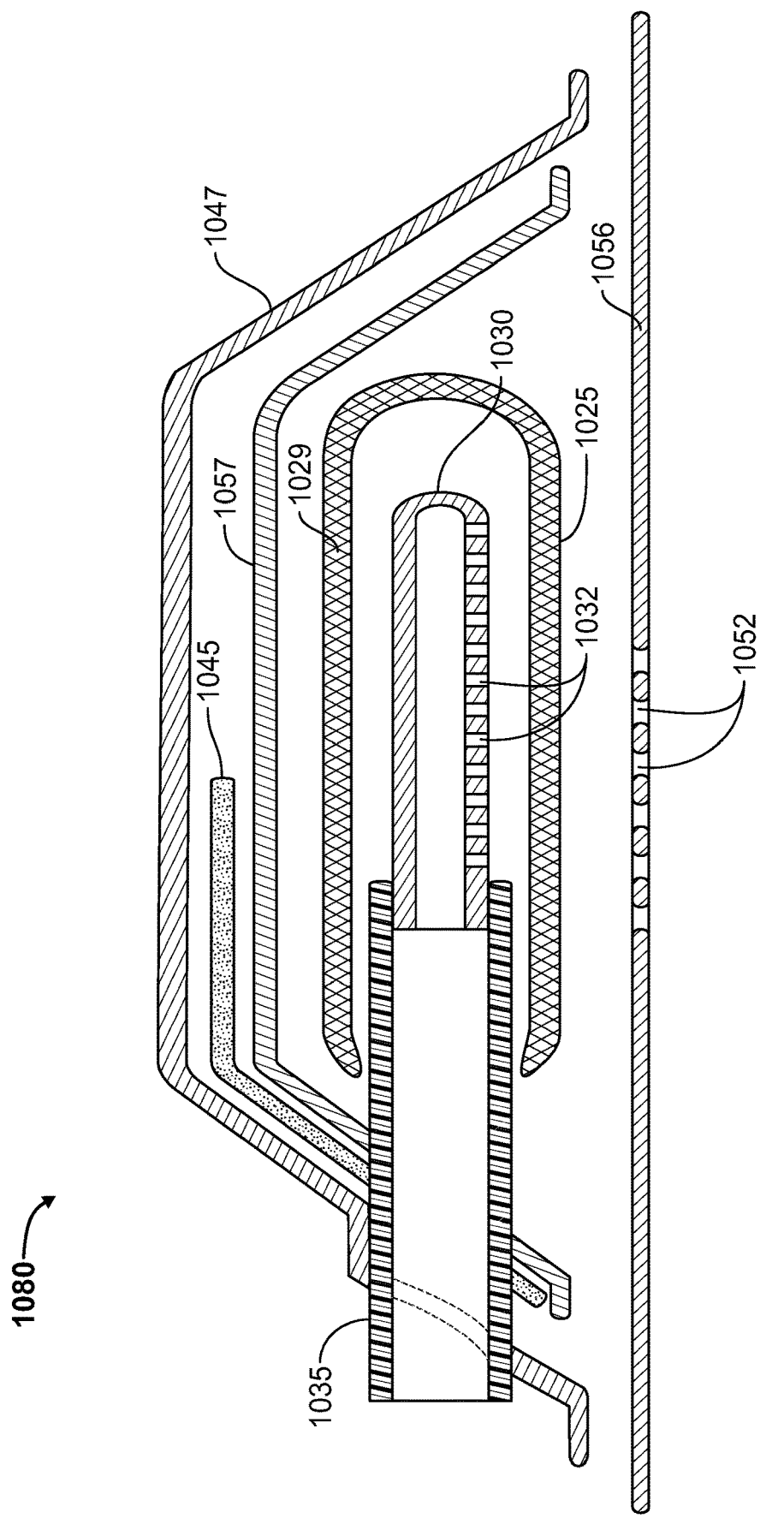
FIGS. 10-11 show exploded, cross-sectional schematic views of layers of components of embodiments of the dressing according to the present invention.
Figure 11:
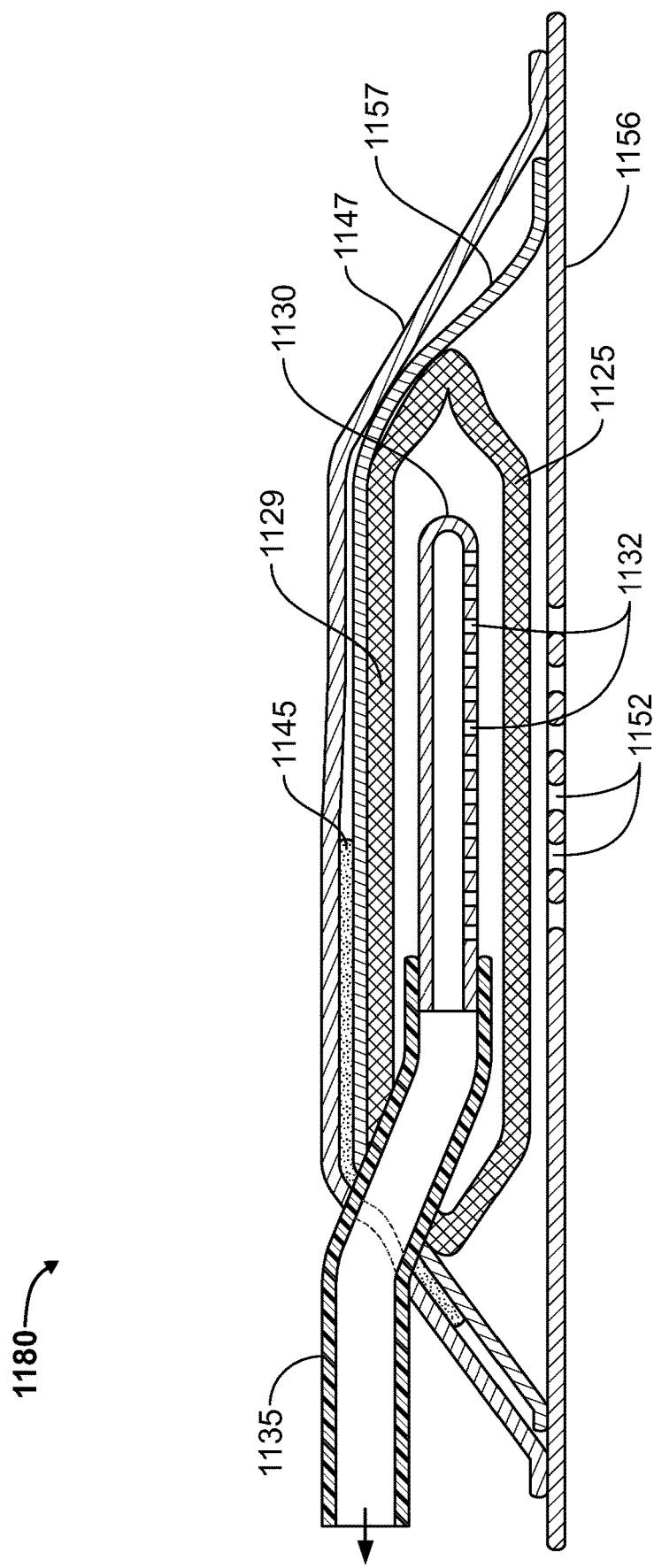

Contour-conforming draping layer 756 of dressing 780 according to the present invention may be directly associated with other components of dressing 780. As portrayed (more explicitly in FIGS. 9-11, presentations in which emphasize components' relative spatial locations), fluid-absorbing/transferring layers 725 and 729, and drain 730 that may be surrounded thereby, may be associated with a surface of contour-conforming draping layer 756. Fluid-absorbing/transferring layer 725, as the lower of layers 725 and 729, may be in physical contact with and lie along the surface of draping layer 756 with which layers 725 and 729 are directly associated.

Contour-conforming draping layer 756 of dressing 780 according to the present invention may feature a set of transverse perforations, the perforations represented by a set of holes 752. Holes 752 represent one or more transverse perforations that may provide access through draping layer 756 from below layer 756 to drain 730 located within fluid-absorbing/transferring layers 725 and 729. Draping layer perforations 752 may be of a range of individual sizes and shapes, and of suitable overall number and geometric arrangement, to provide such access to various configurations of layers 725 and 729 and of drain 730. Draping layer perforations 752 may be variously located along the area of draping layer 756, providing access to layers 725 and 729. The access provided by draping layer perforations 752 may allow transfer of air and fluid between a packed wound-bed (situated below draping layer 756) and drain 730 (situated above draping layer 756).

Draping layer perforation 752 may be a single opening of geometry and area approximating the geometry and area of overlying fluid-absorbing/transferring layer 725. This may facilitate direct contact of all or most of layer 725 with a packed wound-bed independent of intervening section of draping layer 756.

In such embodiments where perforation 752 is a single opening of geometry and area approximating the geometry and area of overlying fluid-absorbing/transferring layer(s) 725, or some other suitable geometry, then the perimeter of fluid-absorbing/transferring layer(s) 725 and/or 729 may be trapped between the draping layer 756 and/or vapor sealant sheet 757. Alternatively, the perimeter of fluid-absorbing/transferring layer(s) 725 and/or 729 may be affixed to draping layer 756 by adhesive on the draping layer or in some suitable fashion. Alternatively, any suitable portion of fluid-absorbing/transferring layer(s) 725 and/or 729 may be affixed to vapor sealant sheet 757 by adhesive on vapor sealant sheet 757 or in some other suitable fashion.

Contour-conforming draping layer 756 of dressing 780 according to the present invention may allow for flexible, airtight adhesion to it of other components of dressing 780. One such component may be a vapor sealant sheet 757.

5. Vapor sealant sheet 757 may overlie all of the area of fluid-absorbing/transferring layer 729. Vapor sealant sheet(s) 757 may be transparent or translucent, providing a view of overlain layer 729, with such transparency/translucency useful in positioning dressing 780 relative to a wound-bed to which it may be applied. Vapor sealant sheet 757 may extend beyond the area of layer 729 to provide a perimeter roundabout the area of layer 729. The perimeter of vapor sealant sheet 757 roundabout layer 729 may flexibly adhere to a surface of draping layer 756 in an airtight fashion. Vapor sealant sheet 757 may be of thickness and of preferably airtight material to serve as an airtight sealing above and roundabout layer 729. Flexible, transparent/translucent, airtight vapor sealant sheet 757 may be of materials including a suitable hydrocolloid material or other suitable material that is non-hydrocolloid.

Airtight vapor sealant sheet 757 may form an airtight seal roundabout layer 729 by adhering directly to the material(s) of the surface of draping layer 756 and/or to other such perimeter-sealed vapor sealant sheets. Additionally or alternatively, airtight vapor sealant sheet 757 may form an airtight seal roundabout layer 729 by adhering to the material(s) of a surface of draping layer 756 (or to other vapor sealant sheets) by means of one or more sealing agents.

Perimeter-sealed vapor sealant sheet 757 may mechanically maintain the placement and orientation of fluid-absorbing/transferring layers 725 and 729 within the larger area of drape 756. Within the area of drape 756, perimeter-sealed vapor sealant sheet 757 may mechanically maintain the placement and orientation of several sets of layers 725 and 729. Dressing 780 according to the present invention may feature several perimeter-sealed vapor sealant sheets 757, each overlying one or more sets of layers 725 and 729.

A vapor sealant sheet 757 may provide an exit for vacuum/drainage tube 735. Maintenance of the airtight seal provided by vapor sealant sheet 757 notwithstanding the presence of the aperture necessitated by vacuum/drainage tube 735 exiting through sheet 757, is dealt with below in the description of tube-anchorage and tube-exit-sealant components 745 and 747.

Contour-conforming draping layer 756 of dressing 780 according to the present invention may feature a variety of shapes, areas and thicknesses to accommodate different types of wounds and NPT conditions. Contour-conforming draping layer 756 may be provided with a set of readily removable backing layer 762. Backing layer 762 may be associated with and protect and preserve tissue-adhesive surface(s) of draping layer 756 until ready for application to a wound-site; such backing layer may prevent unintentional adhesion and/or contamination of draping layer 756. Protective backing layer 762 may be comprised of suitable material including, but not limited, to paper and plastic sheeting.

6. A tube-anchorage and tube-exit-sealant component 745 and/or 747. Tube-anchorage and tube-exit-sealant components 745 and 747 are featured together in FIG. 7C, in an embodiment of dressing 780 according to the present invention in which the functioning of each of components 745 and 747 may reinforce each other. Tube-anchorage and tube-exit-sealant component 745 is featured without component 747 in the embodiment of dressing 780 according to the present invention presented in FIG. 7A; tube-anchorage and tube-exit-sealant component 747 is featured without component 745 in the embodiment of dressing 780 according to the present invention presented in FIG. 7B.

In embodiments of the dressing shown in FIG. 7A-C, either one or both of tube-anchorage and tube-exit-sealant components may mechanically maintain drain 730's placement and orientation within fluid-absorbing/transferring layers 725 and 729. Either one or both tube-anchorage and tube-exit-sealant components may maintain drain 730's placement and orientation preferably by reinforcing the fixation of tube 735 proximal to the tube's (or tubes') exit(s) from sheet 757 overlying layer 729. Such reinforcement may be achieved by the sealing of such tube-anchoring components to other components of the dressing, requiring substantially no contact of the dressing's tube-anchoring components with a patient's tissues.

As presented in FIG. 7A, tube-anchorage and tube-exit-sealant component 745 may provide anchorage for vacuum/drainage tube 735 exiting vapor sealant sheet 757. As portrayed, such tube-anchorage may be provided by component 745 proximally to the exit of tube 735 from sheet 757, by component 745 sealing around and upon the vicinity of the tube-exit aperture in sheet 757. Such tube-anchorage sealing may mechanically contribute to tube-fixity and may confer airtightness to the tube-exit. Such mechanical anchorage of tube 735 may also contribute to maintenance of the placement and orientation of NPT drain(s) 730 within dressing 780. It should be noted that the operation of tube-anchorage and tube-exit-sealant components 745 and 747, respectively, may be enhanced by the application of a preferably pliable putty. Such putty may be applied about the exit point of tube 735 from one or both of tube-anchorage and tube-exit-sealant components 745 and 747.

In certain embodiments, there may be no affixing of fluid-absorbing/transferring layer(s) 725 to draping layer 756 and/or vapor sealant sheet 757 by tube-exit-sealant components 745 and 747. In such embodiments, a seal between tube and vapor sealant sheet 757 may be obtained with a pliable putty, or some other suitable substance, applied at the exit point of tube 735 from vapor sealant sheet.

Tube-anchorage and tube-exit-sealant component 745 may overlie part or all of vapor sealant sheet 757 and may extend beyond sheet 757 in area. Component 745 may be transparent or translucent, providing a view of and through overlain vapor sealant sheet 757. Additionally or alternatively, the area-footprint of component 745 overlying vapor sealant sheet 757 may be sufficiently smaller than the area of sheet 757 that a view of and through transparent/translucent sheet 757 adequate for purposes of positioning dressing 780 may be obtained without need to see below the area-footprint of component 745.

Component 745 may be comprised of one or more materials that confer a suitable range of flexibilities, thicknesses, anchorage-strengths, (transparency/translucency) and airtightness-sealing to the component. Such materials include, but are not limited to, ER Squibb's Duoderm® and 3M's Tegaderm™ or any other suitable hydrocolloid material or any other suitable material which may not be a hydrocolloid material. Component 745 may be sealed onto vapor sealant sheet 757 by adhesion of the materials of component 745 and sheet 757. Additionally or alternatively, component 745 may be sealed onto draping layer 756 by adhering directly to the material(s) of the surface of draping layer 756. Additionally or alternatively, component 745 may be sealed onto vapor sealant sheet 757 and/or draping layer 756 by means of one or more sealing agents.

As presented in FIG. 7B, tube-anchorage and tube-exit-sealant component 747 may provide anchorage for vacuum/ drainage tube 735 exiting vapor sealant sheet 757. As portrayed, such tube-anchorage may be provided by component 747 both proximally to the exit of tube 735 from sheet 757 and along a suitable length of section of tube 735 running over vapor sealant sheet 757 and over draping layer 756. Tube-anchorage and tube-exit-sealant component 747 may provide such anchorage by overlying (and possibly flexibly sealing to) all of the area of vapor sealant sheet 757 and by extending beyond the area of sheet 757 to provide a perimeter roundabout vapor sealant sheet 757. The perimeter of component 747 roundabout the edges of vapor sealant sheet 757 may flexibly adhere to and seal a surface of draping layer 756 roundabout vapor sealant sheet 757. Such perimeter-sealed overlying of vapor sealant 757 may reinforce the airtightness of vapor sealant sheet 757 across its area. Tube-anchorage and tube-exit-sealant component 747 may be transparent or translucent, providing a view of and through overlain vapor sealant sheet(s) 757.

As presented in FIG. 7C, tube-anchorage and tube-exit-sealant components 745 and 747 may both be incorporated into dressing 780, and may both provide anchorage and tube-exit-airtightness for vacuum/drainage tube 735 exiting vapor sealant sheet 757. As presented in FIG. 7C, component 745 may be as described above in FIG. 7A. As presented in FIG. 7C, component 747 may be as described above in FIG. 7B, with the additional functional feature that it may also overlie (and possibly seal with) component 745.

As presented in FIGS. 7B-C, tube-anchorage and tube-exit-sealant component 747 may conform to the section of underlying tube 735, extending the area of tube-exit into a channel, the upper surfaces of which may be defined as part of the lower surface of component 747. The lower surfaces of such tube-exit channel may be defined proximally to the tube-exit aperture in sheet 757 as part of the upper surface of vapor sealant sheet 757 and, beyond the perimeter of 757, by part of the upper surface of drape 756. Component 747 may flexibly adhere to the section of tube 735 running within the tube-exit channel and may seal that section of tube with the other surfaces defining the channel. Additionally or alternatively, such channel may be sealed by means of one or more sealing agent(s).

Component 747 may be comprised of one or more materials that confer a suitable range of flexibilities, thicknesses, transparency/translucency, anchorage-strengths, and airtightness-sealing to the component. Such materials include, but are not limited to, Tegaderm, DuoDerm or any other suitable hydrocolloid material or other suitable non-hydrocolloid material. Component 747 may be sealed onto vapor sealant sheet 757, onto component 745, onto draping layer 756 and/or onto vacuum/drainage tube 735 by adhesion of the materials of component 745 with the materials of those other components. Additionally or alternatively, component 747 may be sealed to any or all of vapor sealant sheet 757, component 745, draping layer 756 and tube 735 by one or more sealing agents.

A dressing 780 according to the present invention may feature a contour-conforming draping layer 756 of dressing 780 may feature, on a given side, both areas of wound-facing surface and areas of non-wound facing surface. Areas of wound-facing surface of such drape layer 756 may be associated with and protected and preserved by sections of backing layer 762. Preferably coterminous with any or all of those areas on either side of such drape 756, but on the reverse-side of such drape 756 from the wound-facing tissue-adhesive surfaced areas that may be associated with protective backing layer 762, areas of non-wound-facing surface of such drape 756 may feature fully assembled, sealed and functional sets of the other non-draping-material components of dressing 780. Each pair of coterminous surfaces on opposite sides of such drape layer 756 may communicate through one or more sets of draping layer perforations 752 as described above.

Figure 8:
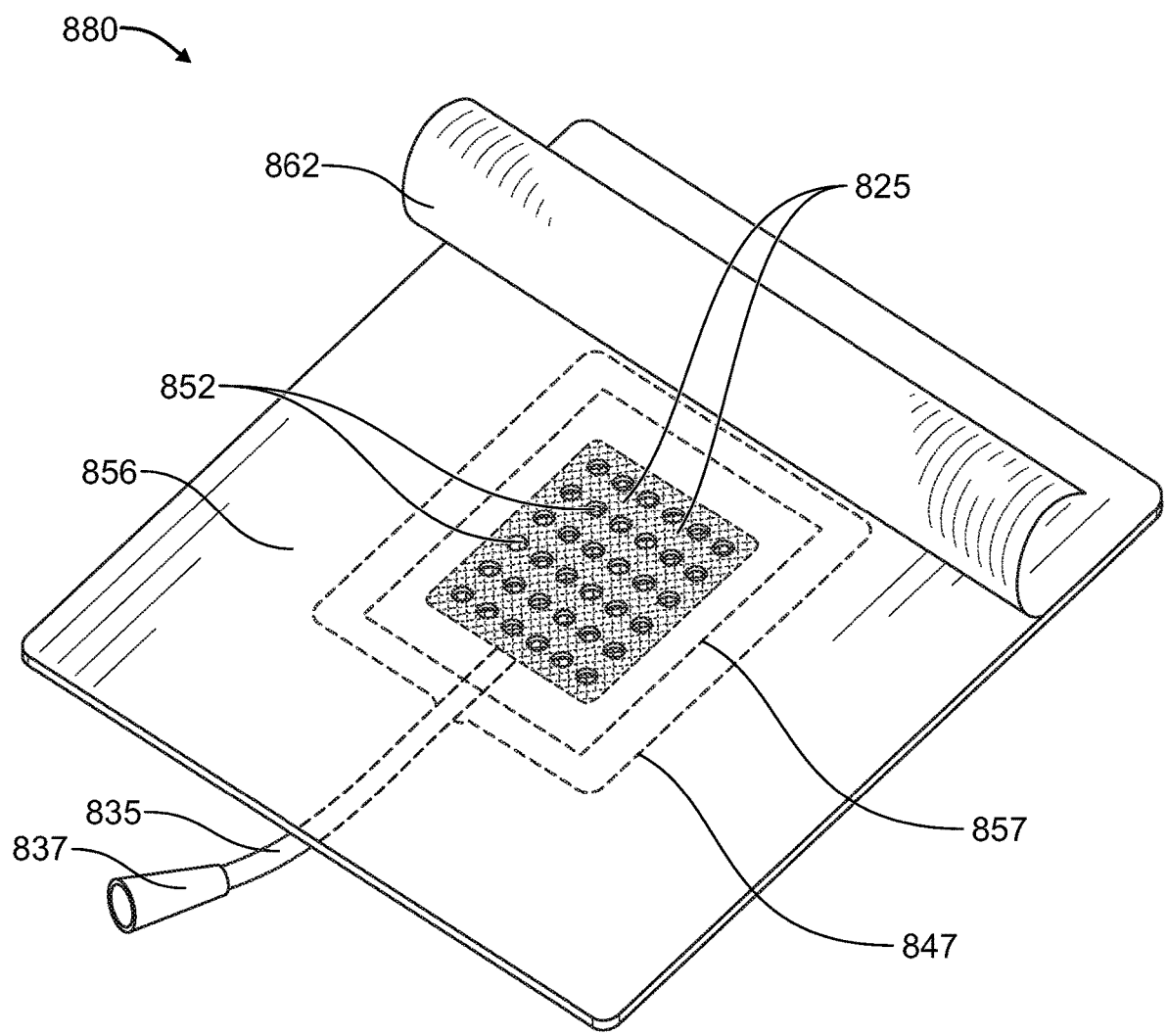
FIG. 8 shows a view from "below" of an embodiment of a dressing according to the present invention.

FIG. 8 is a perspective view from below of an embodiment of a dressing 880 according to the present invention. Protective backing layer 862 is portrayed partially peeled back from the tissue-adhesive face of draping layer 856 to show transverse draping layer perforations 852 running through layer 856, such perforations being representatively nominally centered on the area of layer 856.

On the reverse surface of draping 856, aspects of components that may be in proximal contact with that surface are shown. On the reverse surface of draping 856, representatively shaped area of fluid-absorbing/transferring layer 825 is indicated as extensively overlapped by the area of draping layer perforations 852. Layer 825 is representatively presented as a gauze layer, part of the mesh of which may be directly visible through draping layer perforations 852. Also indicated on the reverse surface of drape 856 are the draped-sealed perimeter of vapor sealant sheet 857 and the draped-sealed perimeter of tube-anchorage and tube-exit-sealant component 847. (The embodiment viewed from below in FIG. 8 may correspond to the embodiments viewed from above in FIGS. 7B-C.)

Indicated as running between sheet 857 and layer 847 along the reverse surface of drape 856 is a section of vacuum/drainage tube 835 proximal to layer 825. Tube 835 is shown exiting the channel formed by part of the reverse surface of drape 856 and part of component 847. A terminus of vacuum/drainage tube 835 and its associated tube-terminus adapter 837 are shown beyond the edge of draping sheet 856.

FIG. 9 is an exploded perspective view from above of an embodiment of a dressing 980 according to the present invention (corresponding to the embodiment in FIG. 7C). From above, the tiered components presented may be:

1. Tube-terminus adapter 937 that may be connected to a terminus of vacuum/drainage tube 935.

2. Vacuum/drainage tube 935 that may run partly under tube-anchorage and tube-exit-sealant component 947 (and then may proceed downward to and/or through other, lower components).

3. Tube-anchorage and tube-exit-sealant component 947 that may be above, and may extend in area beyond the areas of, component 945 and component 957.

4. Tube-anchorage and tube-exit-sealant component 945 (through which tube 935 may run) that may be above component 957.

5. Vapor sealant sheet 957 (through which tube 935 may run) that may be associated at its tube-exit aperture with tube-anchorage and tube-exit-sealant component 945; vapor sealant sheet 957 may be above, and may extend in area beyond the area of, component 929.

6. Fluid-absorbing/transferring layer 929 (through or below which tube 935 may run) that may be above drain 930 and may be continuous with layer 925.

7. NPT drain 930 that may be attached to or may be integrally continuous with vacuum/drainage tube 935; drain 930, which may feature drain perforations 932, may be above layer 925.

8. Fluid-absorbing/transferring layer 925 (through or above which tube 935 may run) that may be above, and may overlie perforations 952 of, draping layer 956.

9. Draping layer 956 that may be below all the above-listed components of dressing 980. Draping layer 956 may be above, and be as extensive in effective area as, component 962.

10. Layer 962 that may be backing the tissue-adhesive surface of layer 956. Protective backing layer 962 may be removed prior to application of dressing 980 to a wound, such that draping layer 956 may be the most wound-proximal component of a dressing 980 applied to a wound.

FIG. 10 and FIG. 11 are exploded, cross-sectional schematic views of embodiments of a dressing according to the present invention.

FIG. 10 schematically portrays in exploded cross-section the components of a dressing 1080 according to the present invention (corresponding to the embodiment in FIG. 9). In FIG. 10, draping layer 1056, with associated perforations 1052, is portrayed as serving as a platform for the other portrayed components. NPT drain 1030, with associated perforations 1032, is portrayed nested between fluid-absorbing/transferring layers 1025 and 1029; NPT drain 1030 is portrayed associated with vacuum/drainage tube 1035. Following along drain-associated tube 1035 away from its association with NPT drain 1030, tube 1035 is portrayed as passing between fluid-absorbing/transferring layers 1025 and 1029, through vapor sealant sheet 1057, through tube-anchorage and tube-exit-sealant component 1045, and through tube-anchorage and tube-exit-sealant component 1047. Tube-anchorage and tube-exit-sealant component 1047 is portrayed as wrapping around tube 1035, such wrapping representing the anchorage and airtightness that either or both tube-anchorage and tube-exit-sealant components 1045 and 1047 may provide.

In FIG. 10, drain-containing fluid-absorbing/transferring layers 1025 and 1029 are portrayed as nested within vapor sealant sheet 1057. Tube-anchorage and tube-exit-sealant component 1045 is portrayed as overlying sheet 1057 proximal to the exit of tube 1035 from sheet 1057, in which vicinity component 1045 may both stabilize fixation of tube-position and contribute to airtight sealing of said tube-exit. Drain 1030, layers 1025 and 1029, sheet 1057, and component 1045 are portrayed as nested within the tube-anchorage and tube-exit-sealant component 1047.

FIG. 11 schematically portrays in exploded cross-section the components of a dressing 1180 according to the present invention (corresponding to the embodiment in FIG. 9). FIG. 11 may present the components presented in FIG. 10 less vertically separated than in FIG. 10. In FIG. 11, draping layer 1156 is portrayed as serving as a platform for the other portrayed components, and as the contact-surface against which some components may be sealed. NPT drain 1130 is portrayed as closely surrounded by fluid-absorbing/transferring layers 1125 and 1129; NPT drain 1130 is portrayed associated with vacuum/drainage tube 1135. Following along drain-associated tube 1135 away from its association with NPT drain 1130, tube 1135 is portrayed as passing between or through fluid-absorbing/transferring layers 1125 and/or 1129, through vapor sealant sheet 1157, through tube-anchorage and tube-exit-sealant component 1145, and through tube-anchorage and tube-exit-sealant component 1147.

In FIG. 11, drain-containing fluid-absorbing/transferring layers 1125 and 1129 are portrayed as closely nested within vapor sealant sheet 1157; layer 1129 is portrayed as closely overlain by vapor sealant sheet 1157. The edges of vapor sealant sheet 1157 that extend beyond sheet 1157's overlying of layer 1129 are portrayed lying along draping layer 1156; vapor sealant sheet 1157 may form airtight seals along the areas of its contact with the surface of draping layer 1156. Tube-anchorage and tube-exit-sealant component 1145 is portrayed as closely overlying vapor sealant sheet 1157 proximal to the exit of tube 1135 from vapor sealant sheet 1157, in which vicinity component tube-anchorage and tube-exit-sealant component 1145 may both stabilize fixation of tube-position (and, thereby, stabilize fixity of drain-position) and contribute to airtight sealing of said tube-exit.

In FIG. 11, tube-anchorage and tube-exit-sealant component 1145 and vapor sealant sheet 1157 are portrayed as closely overlain by tube-anchorage and tube-exit-sealant component 1147. The edges of tube-anchorage and tube-exit-sealant component 1147 that extend beyond components 1147's overlying of component 1145 and of fluid-absorbing/transferring layer 1129 are portrayed lying along draping layer 1156; tube-anchorage and tube-exit-sealant component 1147 may form airtight seals along the areas of its contact with the surface of draping layer 1156.

As per the portrayals in FIG. 11 and the descriptions presented in FIGS. 7-10 of components' features and functions, the tube-exit from the interior to the exterior of dressing 1180 may be sealed by tube-anchorage and tube-exit-sealant component 1145 and/or by tube-anchorage and tube-exit-sealant component 1147 (either or both, possibly, by means of sealing agent(s)); airtight component 1147 may closely overlie component 1145 and vapor sealant sheet 1157; airtight component 1147 may be sealed at its edges against the surface of draping layer 1156 (possibly by means of sealing agent(s)); airtight vapor sealant sheet 1157 may overlie fluid-absorbing/transferring layers 1125 and 1129, closely overlying layer 1129; airtight vapor sealant sheet 1157 may be sealed at its edges against the surface of draping layer 1156 (possibly by means of sealing agent(s)); the airtight material(s) of draping layer 1156 may underlie drain-containing fluid-absorbing/transferring layers 1125 and 1129, closely underlying layer 1125. Thus, air/fluid-flow access to drain 1130 from the exterior of dressing 1180 may be obtained only via draping layer 1156's perforations 1152 and through vacuum/drainage tube 1135.

The portrayed drain-distal terminus of vacuum/drainage tube 1135 displays an outward-directed arrow. The arrow may indicate the direction within tube 1135 of outward flow of air and/or fluid. Such air/fluid-flow may originate exterior to dressing 1180 along the wound-facing surface of draping layer 1156; may traverse draping layer 1156 to the non-wound-facing surface of draping layer 1156 through its associated perforations 1152; may travel via fluid-absorbing/transferring layers 1125 and 1129 to the interior of drain 1130 through its associated perforations 1132; and, from the interior of drain 1130, may travel to the exterior of dressing 1180 via vacuum/drainage tube 1135. When applied to a wound, the dressing as schematically represented in FIG. 11 as 1180 would have draping layer 1156 overlying and sealing a wound-bed. Flow of air and/or of wound-fluid exudate from the wound-bed may then follow the route outlined above, passing through draping layer perforations 1152 to travel into drain 1130 and then outward through tube 1135.

Dressing 1180 according to the present invention may feature modalities beyond the standard application of negative pressure to wound-beds and drainage of wound-fluid exudate from wound-beds. Among those modalities may be capabilities of wound-flushing, possibly via multi-lumen tube(s) 1135. Such capability may allow for reversal of the standard direction of fluid flow. Such capability of reverse-flow may be utilized to selectively deliver medicinal or other fluids to a sealed wound-bed at a pause between NPT sessions of a course of NPT; or to partially irrigate a sealed wound-bed to wet its packing material and wound-bed surfaces (possibly with surfactants) prior to a wound-dressing change upon the conclusion of a course of NPT.

As reverse-flow modalities may be mediated by vacuum/drainage tube 1135, they and several other non-standard advantages of use of dressings according to the present invention over conventional apparatus and methods may be addressed in the description of vacuum/drainage tube 735 of FIGS. 7A-C.

As portrayed in FIG. 11, fixation of position of vacuum/drainage tube 1135 (and, thereby, fixation of position of NPT drain 1030) may be stabilized by tube-anchorage and tube-exit-sealant component 1145 and/or tube-anchorage and tube-exit-sealant component 1147. Those tube-anchorage and tube-exit-sealant components may also contribute to the airtightness of dressing 1180, particularly at and/or along the tube-exit of vacuum/drainage tube 1135 from the interior to the exterior of dressing 1180. The functionality of tube-anchorage and tube-exit-sealant component 1145 and tube-anchorage and tube-exit-sealant component 1147 may be attained by the sealing of those components exclusively to other components of dressing 1180, with no contact with patients' skin or other tissues.

Figure 12:
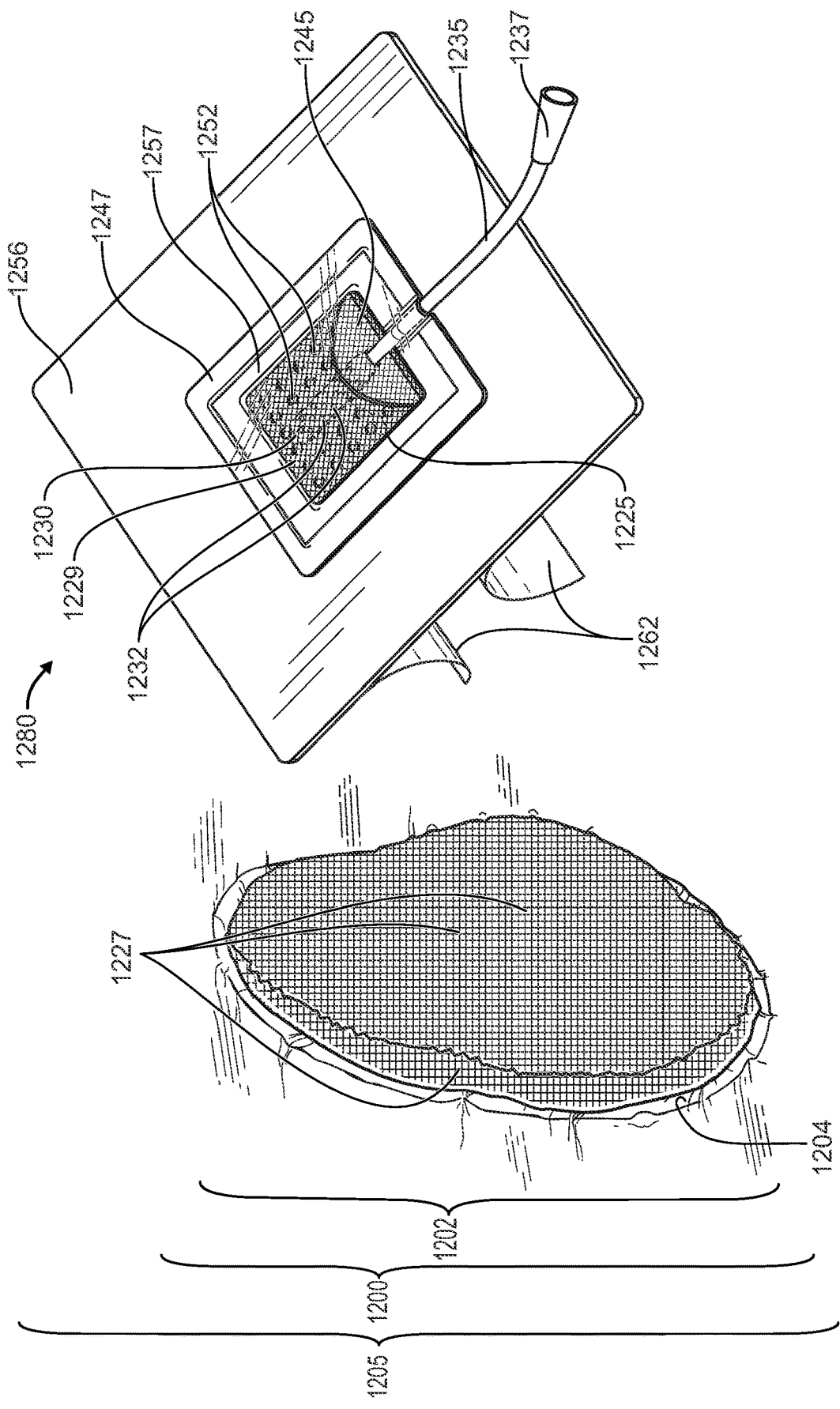
FIGS. 12-14 show embodiments of the dressing according to the present invention (as per FIGS. 7-11) in conjunction with a representative wound (the latter, as per FIGS. 1-2).
Figure 13:
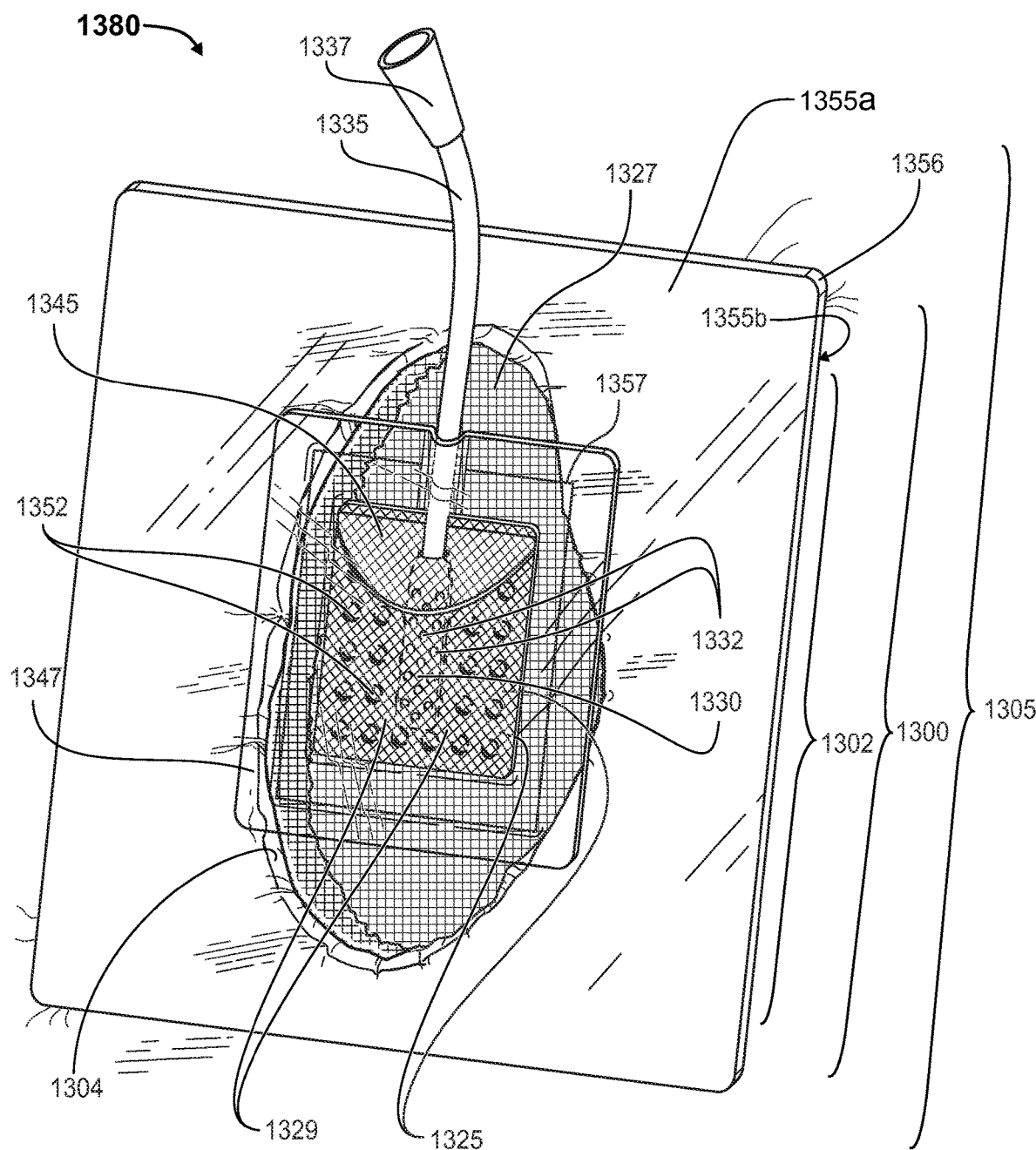
Figure 14:
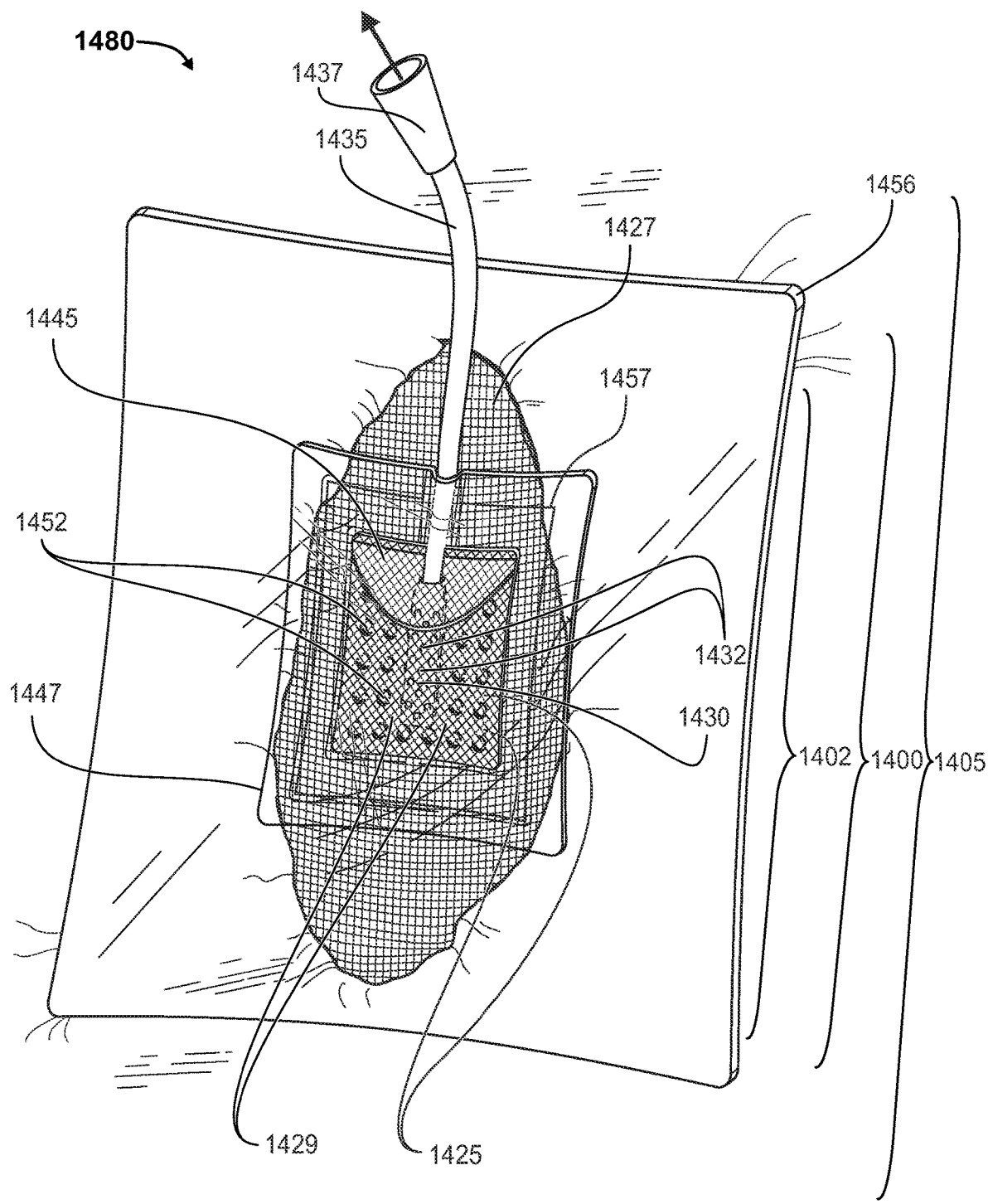

FIGS. 12-14 return to the perspective view utilized in FIGS. 1-9, linked to the assumed directionality of illumination and the orientation of the viewer given in description of FIG. 1. FIGS. 12-14 are perspective views from above of embodiments of a dressing according to the present invention (as per FIGS. 7-11) in conjunction with a representative wound (the latter, as per FIGS. 1-2).

FIG. 12 is a perspective view from above of an embodiment of a dressing 1280 according to the present invention, in conjunction with a representative wound-bed 1202 that may be ready for application of dressing 1280. As portrayed, wound-bed 1202 may be proximally surrounded by a perilesional area 1200; both wound-bed 1202 and surrounding perilesional area may be contained within a wider wound-site 1205.

In FIG. 12, wound-bed 1202 is portrayed ready for application of dressing 1280, such state of readiness attained by preparation of wound-bed 1202 and of an appropriate portion of wider wound-site 1205 beyond wound-bed 1280. Initial preparation of wound-bed 1202 and of wider wound-site 1205 beyond wound-bed 1280 prior to the stage portrayed in FIG. 12 may be representatively portrayed in FIGS. 1-2 and detailed in the corresponding descriptions of FIGS. 1-2. In FIG. 12, wound-bed 1202 is portrayed as having been further readied for application of dressing 1280 by the expedient of wound-packing, with packing material within wound-bed 1202 designated as 1227.

A precautionary accommodation that may have been made in packing wound-bed 1202 with packing material 1227 as part of preparing wound-bed 1202 for application of dressing 1280, may have been a slight under-packing of wound-bed 1202. Such under-packing of prepared wound-bed 1202 is depicted in FIG. 12 by packing material 1227 portrayed as almost but not completely filling wound-bed 1202. Uppermost edges of wound-walls 1204 of slightly under-packed, almost completely filled wound-bed 1202 are shown as not covered by packing material 1227. (Wound-walls 1204 may be continuous roundabout the entire inner perimeter of wound-bed 1202. Given the perspective view utilized, sections of right wound-wall 1204 may be blocked from view by the perilesional upper edge of right wound-wall 1204.)

In FIG. 12, packing material 1227 is portrayed as comprised of layers of gauze. The right-most region of packing material 1227 is portrayed as the uppermost layer of packing material 1227 within prepared, slightly under-packed wound-bed 1202. Depiction of wound-packing material 1227 as gauze is not limiting; dressing 1280 may be applied to and used in treating wound-beds filled or packed with materials other than gauze, e.g. foam or other suitable material.

The portrayed dressing 1280 is representative of a range of such dressings differing in the size, shape, capabilities, characteristics, numbers and/or relative orientations of their constituent components. Such variation may be in any or all of, but not limited to, draping layer 1256, draping layer perforations 1252, NPT drain 1230, drain perforations 1232, fluid-absorbing/transferring layers 1225 and 1229, vapor sealant sheet 1257, tube-anchorage and tube-exit-sealant component 1245, tube-anchorage and tube-exit-sealant component 1247, vacuum/drainage tube 1235, and drain-distal tube-terminus adapter 1237. Description of the range of such variations in such constituent components of NPT drain 1280 may be addressed, partially and representatively, in the description of constituent components of NPT drain 780 of FIGS. 7A-C.

One of the sets of choices made in selecting dressing 1280 may have been as to the lumen number and functional capabilities of vacuum/drainage tube 1235. Linked to that set of choices may have been selection for the number, size, shape, capacity and functional capabilities of NPT drain 1230, along with the number and characteristics of drain-distal tube-terminus adapter 1237.

The material of draping layer 1256 well beyond the borders of tube-anchorage and tube-exit-sealant component 1247 (or, for dressings 1280 lacking such tube-anchorage and tube-exit-sealant component 1247, well beyond the borders of vapor sealant sheet 1257) may have been selectively trimmed to accommodate the body location and contouring of wider wound-site 1205. (Such trimming of the material of draping layer 1256 may be carried out with consideration of the area of tissue-adhesive surface of such material required to effect an airtight NPT seal roundabout wound-bed 1202 upon application of dressing 1280 to wound-site 1205.)

FIG. 12 portrays dressing 1280 with backing layer 1262 protective of the wound-facing tissue-adhesive broad surface of draping layer 1256 having been partly removed. Procedurally, backing layer 1262 may be completely removed from wound-facing tissue-adhesive surface(s) of draping layer 1256 prior to application of dressing 1280 to prepared wound-bed 1202 and to an appropriate portion of wider wound-site 1205 beyond wound-bed 1202.

Additional steps may be taken before application of the dressing 1280 to wound-bed 1202 and to an appropriate portion of wider wound-site 1205 beyond wound-bed 1202. The additional steps may include finalization of selection of the positioning and orientation of dressing 1280 relative to wound-bed 1202. Tissue-adhesive characteristics of the wound-facing surface of draping layer 1256 may allow dressing 1280 to be removed, repositioned and re-applied several times before finalization of application to wound-bed 1202 and to the finalized dressing-covered portion of wider wound-site 1205 beyond wound-bed 1202 for a given course of NPT; tissue-adhesive characteristics of the wound-facing surface of draping layer 1256 may allow dressing 1280 to be removed, repositioned and re-applied to wound-site 1205 between NPT sessions of a given course of NPT.

The position and orientation of an NPT drain 1230 within a dressing 1280 may be labeled through visible/tactile marking(s) that may be readily perceived on or through the uppermost surface of a dressing 1280. With fluid absorbing/transferring layer 1229 possibly blocking NPT drain 1230 from view through the transparent/translucent overlying layer(s), such indication of position and orientation of an NPT drain 1230 within a dressing 1280 may be useful in positioning and orienting the dressing during its application to wound-site 1205.

FIG. 13 is a perspective view from above of an embodiment of a dressing 1380 according to the present invention, as representatively applied to a representative wound-bed 1302 and to an appropriate portion of a wider wound-site 1305 beyond wound-bed 1302. FIG. 13 distinguishes between the lower, wound-facing tissue-adhesive surface of draping layer 1356 (designated as wound-facing surface 1355*b*) and the upper, non-wound-facing surface of draping layer 1356 (designated as non-wound-facing surface 1355*a*). FIG. 13 portrays representative positioning and orientation of dressing 1380 relative to wound-bed 1302 and to the wider wound-site 1305 beyond wound-bed 1302. The portrayed positioning and orientation of dressing 1380 with respect to relevant features of wound-bed 1305, display several features of diverse roles and levels of significance relative to the functionality of dressing 1380:

Extensive contact-area of tissue-adhesive wound-facing surface 1355*b* with the tissue-surface of wound-site 1305 roundabout wound-bed 1302, inclusive of perilesional area 1300.

Extensive overlap of the area of draping layer perforations 1352 with the area of packing material 1327 within wound-bed 1302. (The term "area of draping layer perforations" as used herein refers to the area across the broad surface of the draping layer occupied by the transverse perforations through the draping layer, with inclusion of the areas between individual perforations. In the portrayal in FIG. 13, the area of draping layer perforations 1352 is depicted as closely bounded from without by the area of fluid-absorbing/transferring layer 1329.)

Approximate centering of the area of draping layer perforations 1352 on the area of wound-packing material 1327 within wound-bed 1302.

Approximate orientation of NPT drain 1330 along the long axis of wound-bed 1302.

Orientation of vacuum/drainage tube 1335 relative to wound-site 1305.

The extent of contact of tissue-adhesive wound-facing surface 1355*b* with the tissue-surface of wound-site 1305 roundabout wound-bed 1302, and the extent and geometry of overlap of the area of draping layer perforations 1352 with the area of packing material 1327 within wound-bed 1302, may be factors to have been taken into consideration in selecting a dressing 1380 of specific characteristics. Relevant characteristics may include the sizes and shapes of draping layer 1356, of fluid-absorbing/transferring layers 1325 and 1329, and of the area of draping layer perforations 1352. As constrained by wound-site 1305's contours and proximal body-parts, an extensive and close interface of contact between wound-facing surface 1355*b* and the patient's tissue-surface may contribute to obtaining an NPT-required quality of airtight sealing roundabout wound-bed 1302. With wound-site 1305's local conditions of moistness as a factor that may have to be contended with, other characteristics that may have been selected relative to obtaining a high quality interface of dressing 1380 with wound-site 1305, may include the tissue-adhesion characteristics of wound-facing surface 1355*b*.

With an appropriately selected dressing 1380 in hand, the practitioner may have taken into consideration in initial positioning and orienting of the dressing for its application to wound-site 1305, the attainment of extensive contact of tissue-adhesive wound-facing surface 1355*b* with the tissue-surface of wound-site 1305 roundabout wound-bed 1302. Likewise, in such initial positioning and orienting of the dressing, the practitioner may have considered attainment of an extensive overlap of the area of draping layer perforations 1352 with the area of packing material 1327. Other considerations for such initial, coarse adjustments of general positioning and orientation may include suitability of the direction of vacuum/drainage tube(s) 1335 and drain-distal tube-terminus adapter(s) 1337, relative both to proximal body-parts and to the NPT vacuum controller and/or other treatment control-and-monitor equipment.

In making fine adjustments for precise positioning and orientation of dressing 1380 prior to finalizing its application to wound-site 1305, the practitioner may have been guided by considerations of attainment of an overlap of the area of draping layer perforations 1352 with the area of packing material 1327 within wound-bed 1302, and of a particular orientation of NPT drain 1330 within that geometry. As portrayed in FIG. 13, the area of draping layer perforations 1352 may be approximately centered on the area of packing material 1327 within wound-bed 1302. In addition, FIG. 13's portrayal of a representatively applied dressing 1380 shows no overlying of draping layer perforations 1352 upon perilesional area 1300; the outer edges of the area of draping layer perforations 1352, as portrayed in FIG. 13, may be well within wound-walls 1304, with a perimeter of packing material 1327 visible roundabout the area of draping layer perforations 1352, showcasing a lateral gap between draping layer perforations 1352 and surrounding perilesional area 1300.

As per the dressing-internal spatial relationships among components of dressings 980, 1080 and 1180 portrayed in FIGS. 9, 10 and 11, respectively, draping layer perforations 1352 on non-wound-facing surface 1355*a* may be directly overlain by fluid absorbing/transferring layer 1325 that may be directly overlain by NPT drain 1330; during NPT sessions, negative pressure may be applied to wound-bed 1302 via NPT drain 1330's drain perforations 1332. Thus, NPT negative pressure may be most directly applied to packing material 1327 within wound-bed 1302, and drainage of wound-fluid exudate may be most directly effected, in the region of overlap of the area of packing material 1327 with the area of draping layer perforations 1352.

A high degree of overlap of the two areas close to their mutual centers may yield an evenly balanced drainage of wound-fluid exudate from all parts of packing material 1327 within wound-bed 1302 under NPT conditions. Mutual centering of the areas may contribute to an even distribution of contraction of wound-walls 1304 under NPT conditions, which may positively impact rapidity and quality of wound-healing. Minimization of overlying of drain layer perforations 1352 upon perilesional area 1300 may minimize contact of wound-fluid exudate with tissues of perilesional area 1300 during NPT sessions; such contact, particularly under NPT conditions, may be deleterious to tissue health. Thus, the extent and geometry of overlap of the area of draping layer perforations 1352 with the area of packing material 1327 within wound-bed 1302 may impact the effectiveness of exudate-drainage, quality of wound-closure, and health of perilesional area 1300.

An additional consideration during fine adjustments for precise positioning and orientation of dressing 1380 prior to finalizing its application to wound-site 1305, particularly for surgical wounds, may have been the orientation of NPT drain 1330 relative to the geometry of wound-bed 1302. In FIG. 13, NPT drain 1330 is portrayed as oriented approximately along the long axis of wound-bed 1302, as delimited by surrounding wound-walls 1304. Wound-bed healing may naturally tend to preferentially promote wound-closure orthogonal to particular cleavage lines (such as Langer's, Kraissl's or Borges's cleavage lines) that lie along particular orientations in different regions of the body. Particularly in surgical wounds, where incisions may have been made parallel to such cleavage lines to take advantage of the preferential directionality of natural wound-closure in a given region of the body, approximate alignment of the NPT drain 1330 with the wound-axis of wound-bed 1302 may be advantageous to the wound-healing process. (Such orientation of NPT drain 1330 as portrayed in FIG. 13 is representative and not limiting; NPT drain(s) 1330 of dressing 1380 according to the present invention may be associated with a wide range of wound-bed shapes, including those with no discernable long axis, such as circular wounds and various irregular wounds. Orientation and location of NPT drain 1330 within wound-bed 1302 may be constrained by many clinical factors, even in the case of surgical wounds; such factors may include the three-dimensional shape of the volume of wound-bed 1302 and the specifics of the contouring of wider wound-site 1305.)

In application to wound-site 1305 of dressing 1380 according to the present invention, establishment of the position and orientation of dressing 1380 relative to relevant features of wound-bed 1305, including the geometry of wound-bed 1302, may have been straightforward, as may be portrayed in FIG. 13.

With comprehensive visual knowledge of wound-site 1305 obtained through transparent/translucent tube-anchorage and tube-exit-sealant component(s) 1347 (and/or 1345), and/or through transparent/translucent vapor sealant sheet 1357, and through transparent/translucent draping layer 1356; with visual/tactile marking(s) of the position and orientation of NPT drain(s) 1330 within dressing 1380, perceivable on or through overlying component(s) 1347 (and/or 1345) and/or overlying sheet 1357; with edges of all or any of component(s) 1347 (and/or 1345), of sheet 1357, of fluid absorbing/transferring layer 1329, and of layer 1356, perceivable relative to geometries of relevant features of wound-site 1305 during application of dressing 1380, the practitioner may have established a set of position and orientation of dressing 1380 with relative ease and precision. Maintenance of the position and orientation of applied dressing 1380 may be effected by the tissue-adhesion characteristics of wound-facing surface 1355b. Establishment and maintenance of mutual positions and orientations of constituent components within applied, positioned and oriented dressing 1380, may be obtained as consequences of the set of structural functionalities of those components preassembled with fixity of position and of orientation within dressing 1380.

In FIG. 13, draping layer 1356 of dressing 1380 may be conformed and adhered to the contours of perilesional area 1300 and of the rest of dressing-covered regions of wound-site 1305. Practitioner manipulation across non-wound-facing surface 1355a, smoothing draping layer 1356 over the underlying contours, may have been readily accomplished and may have been guided and facilitated by the transparency/translucency of draping layer 1356.

As shown in FIG. 13, the contact-area of tissue-adhesive wound-facing surface 1355b with the tissue-surface of wound-site 1305 roundabout wound-bed 1302, inclusive of perilesional area 1300, may be extensive. FIG. 13's portrayal of an applied dressing 1380 shows no perilesional area 1300 not overlain by draping layer 1356; in addition, extensive regions of the wider wound-site 1305 beyond perilesion area 1300 may be overlain, and conformed to, by the material of draping layer 1356, and adhered to by tissue-adhesive wound-facing surface 1355b. The extent and quality of the contact-area of tissue-adhesive wound-facing surface 1355b with the tissue surface roundabout wound-bed 1302, may impact production of effective airtight perimeter sealing of wound-bed 1302 under NPT conditions of low wound-bed air pressure.

FIG. 14 is a perspective view from above of an embodiment of a dressing 1480 (corresponding to the embodiment in FIG. 13) representatively applied, conformed and adhered to a representative prepared wound-site 1405, under NPT conditions of low air pressure within wound-bed 1402. The portrayed tube-terminus adapter 1437 of vacuum/drainage tube 1435 displays an outward-directed arrow. The arrow may indicate airtight connection of tube-terminus adapter 1437 to a functioning NPT vacuum controller (not shown) and/or suitable connections for obtaining wound-bed NPT conditions by mean of other treatment control-and-monitor equipment (not shown); such other treatment control-and-monitor equipment may facilitate also such non-standard functionalities of representative dressing 1480 according to the present invention as may be addressed, partially and representatively, in the description of vacuum/drainage tube 735 of FIGS. 7A-C.

In FIG. 14, the outward-directed arrow associated with tube-terminus adapter 1147 may indicate, also, the direction of exudate-flow within vacuum/drainage tube 1435 outward from wound-bed 1402; such outward flow may be consequent to NPT conditions of partial vacuum obtaining within wound-bed 1402. Those conditions may be produced by an NPT vacuum controller (or an operational vacuum-functionality of other suitable treatment control-and-monitor equipment) connected to tube-terminus adapter 1437, acting through vacuum/drainage tube 1435 upon the interior of NPT drain 1430; through drain perforations 1432, acting upon fluid-absorbing/transferring layers 1425 and 1429; through draping layer perforations 1452, acting upon and within packing material 1427 within wound-bed 1402.

NPT conditions of partial vacuum obtaining within packing material 1427 may contract packing material 1427 and may subject the wound-base and wound-walls of wound-bed 1402 to the effects of such negative pressure. Such effects may include the drawing out of wound-fluid exudate from the wound-base and wound-walls of wound-bed 1402 into and through packing material 1427; wound-fluid exudate in packing material 1427 may retrace the path of application of partial vacuum, flowing up and out of wound-bed through vacuum/drainage tube 1435.

With the contraction of packing material 1427 and the application of partial vacuum to the wound-base and wound-walls of wound-bed 1402, wound-bed 1402 may be contracted; as portrayed in FIG. 14, wound-bed 1402 may be smaller than the same-scale portrayal of wound-bed 1302 of FIG. 13, particularly orthogonal to, and approximately symmetrically medially toward, the long axis of wound-bed 1402, along which NPT drain 1430 may be centered and oriented. In FIG. 14, the edges of perilesional area 1400 proximal to wound-bed 1402 are portrayed as pulled inward toward the center of wound-bed 1402, mostly medially toward the long axis of wound-bed 1402; skin-tension lines in perilesional area 1400 proximal to wound-bed 1402 may indicate the mainly medial stretching of the upper edges of the wound-walls toward contracted wound-bed 1402. Regions of wider wound-site 1405 beyond perilesional area 1400 may, as portrayed in FIG. 14, be somewhat distorted as consequent to NPT conditions of partial vacuum obtaining within wound-bed 1402.

Contraction of wound-bed 1402 vertically downward along the viewer's line-of-sight, may also typically occur under NPT conditions of partial vacuum obtaining within wound-bed 1402. In FIG. 14, draping layer 1456, particularly above contracted wound-bed 1402, may be pulled downward into the depth of wound-bed 1402, pressed against contracted packing material 1427; packing material 1427 may be portrayed distorted (relative to the portrayal of packing material 1327 of FIG. 13), compressed within the vacuum-reduced volume of wound-bed 1402. Likewise, through a set of distortions of their area-borders (relative to their portrayals in FIG. 13), FIG. 14 shows the distortions medially inward and vertically downward of tube-anchorage and tube-exit-sealant components 1447 and 1445, of vapor sealant sheet 1457, and of fluid-absorbing/transferring layers 1429 and 1425. Likewise, vacuum/drain tube 1435 proximal to its exit from below tube-anchorage and tube-exit-sealant component 1447, and following along the tube-exit channel beneath component 1447 in the direction of the viewer's station beyond and approximately in line with the figure's "FIG. 14," may be distorted downward toward NPT drain 1430. Depending on the characteristics of flexibility of NPT drain 1430, NPT drain 1430 may be distorted by NPT conditions of partial vacuum obtaining within wound-bed 1402.

The wound-base and wound-walls of wound-bed 1402 may be under mechanical strain consequent to NPT conditions of partial vacuum ("NPT negative pressure") obtaining within wound base 1402. While such strain may be contributory to NPT-enhancement of wound-healing, the intensity of the strain may need to be limited to accommodate the sensitivities and strengths of the tissues of the wound-base and wound-walls of wound-bed 1402. NPT sessions featuring NPT drain 1430 according to the present invention applied to a prepared wound-site 1405, may accelerate NPT-enhancement of wound-healing without over-straining wound-walls and wound-base tissues of wound-bed 1402.

Thus, apparatus and methods that streamline and simplify preparing a wound-site for negative pressure treatment have been provided. Persons skilled in the art will appreciate that the present invention can be practiced by other than the described embodiments, which are presented for purposes of illustration rather than of limitation, and that the present invention is limited only by the claims that follow.

The invention claimed is:

1. A wound dressing comprising:
a wound-fluid drain for use in negative pressure wound treatment ("NPT drain");
a vacuum/drainage tube comprising a terminus associated with the NPT drain, said NPT drain being configured to non-simultaneously withdraw fluid from a wound and deliver fluid to the wound;
fluid-absorbing/transferring layer for distributing negative pressure from the NPT drain, said fluid-absorbing/transferring material being in contact with the NPT drain;
a vapor sealant sheet formed from a hydrocolloid material, the vapor sealant sheet that overlies the fluid-absorbing/transferring layer, said vapor sealant sheet comprising an adhesive located over at least a central zone of a wound-facing surface of the vapor sealant sheet, the adhesive for adhering the vapor sealant sheet to the fluid-absorbing/transferring layer, said adhesive that mechanically maintains the placement and orientation of fluid-absorbing/transferring layer relative to the vapor sealant sheet; and
a tube-anchorage component that is in contact with at least a portion of the vapor sealant sheet and a portion of the fluid-absorbing/transferring layer, the tube-anchorage component for mechanically maintaining placement of the NPT drain relative to the fluid-absorbing/transferring layer.

2. A wound dressing comprising:
a wound-fluid negative pressure treatment ("NPT") drain;
a vacuum/drainage tube comprising a terminus associated with the NPT drain;
fluid-absorbing/transferring layer for distributing negative pressure from the vacuum/drainage tube, said fluid-absorbing/transferring layer being in contact with the vacuum/drainage tube;
a vapor sealant sheet formed from a hydrocolloid material, the vapor sealant sheet that overlies the fluid-absorbing/transferring layer, said vapor sealant sheet comprising an adhesive located over at least a central zone of a wound-facing surface of the vapor sealant sheet, the adhesive for adhering the vapor sealant sheet to the fluid-absorbing/transferring layer, said adhesive that mechanically maintains the placement and orientation of the fluid-absorbing transferring layer relative to the vapor sealant sheet;
a first tube-anchorage component that is in contact with at least a portion of the vapor sealant sheet; and
a second tube-anchorage component, the first and second tube-anchorage components for mechanically maintaining the NPT drain's placement relative to the fluid-absorbing/transferring layer.

3. A wound dressing comprising:
a vacuum/drainage tube comprising a terminus;
a fluid-absorbing/transferring layer for distributing negative pressure from the vacuum/drainage tube, said fluid-absorbing/transferring layer being in contact with the vacuum/drainage tube;
a vapor sealant sheet formed from a hydrocolloid material, the vapor sealant sheet that overlies the fluid-absorbing/transferring layer, said vapor sealant sheet comprising an adhesive located over at least a central zone of a wound-facing surface of the vapor sealant sheet, the adhesive for adhering the vapor sealant sheet to the fluid-absorbing/transferring layer, said adhesive that mechanically maintains the placement and orientation of the fluid-absorbing transferring layer relative to the vapor sealant sheet; and
a tube-exit-sealant component for mechanically maintaining the vacuum/drainage tube's placement relative to the fluid-absorbing/transferring layer.

4. The wound dressing of claim 1 wherein the fluid-absorbing/transferring layer comprises gauze.

5. The wound dressing of claim 1 wherein the fluid-absorbing/transferring layer comprises foam.

6. The wound dressing of claim 1 wherein the fluid-absorbing/transferring layer comprises an upper layer and a lower layer.

7. The wound dressing of claim 6 wherein the NPT drain is enfolded between the lower layer and the upper layer.

8. The wound dressing of claim 2 wherein the vacuum/drainage tube comprises a plurality of lumens.

9. The wound dressing of claim 8 wherein the plurality of lumens comprises at least one lumen configured to deliver fluid to a wound and at least one lumen configured to withdraw fluid from the wound.

10. The wound dressing of claim 8 wherein at least one lumen is configured to convey a medical device.

11. The wound dressing of claim 3 wherein the vacuum/drainage tube terminus is associated with a negative pressure treatment ("NPT") drain.

12. The wound dressing of claim 11 wherein the NPT drain comprises a plurality of NPT drains.

13. The wound dressing of claim 3 wherein the vacuum/drainage tube is further associated with an external vacuum source.

\* \* \* \* \*